(12) United States Patent
Shimamura

(10) Patent No.: US 11,189,025 B2
(45) Date of Patent: Nov. 30, 2021

(54) DYNAMIC IMAGE ANALYSIS APPARATUS, DYNAMIC IMAGE ANALYSIS METHOD, AND RECORDING MEDIUM

(71) Applicant: Konica Minolta, Inc., Tokyo (JP)

(72) Inventor: Kenta Shimamura, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 215 days.

(21) Appl. No.: 16/512,800

(22) Filed: Jul. 16, 2019

(65) Prior Publication Data

US 2020/0034964 A1 Jan. 30, 2020

(30) Foreign Application Priority Data

Jul. 24, 2018 (JP) .............................. JP2018-138096

(51) Int. Cl.
*G06T 7/00* (2017.01)
*G06T 7/20* (2017.01)

(52) U.S. Cl.
CPC .............. *G06T 7/0012* (2013.01); *G06T 7/20* (2013.01); *G06T 2207/10116* (2013.01); *G06T 2207/30104* (2013.01)

(58) Field of Classification Search
CPC ....... G06T 7/0012; G06T 7/20; G06T 7/0016; G06T 2207/30104; G06T 2207/10116; G06T 2207/20021; G06T 2207/10016; A61B 6/486; A61B 6/504
See application file for complete search history.

(56) References Cited

U.S. PATENT DOCUMENTS

| 5,048,534 | A | * | 9/1991 | Marinus | ............... | H04N 5/3205 600/504 |
| 2009/0097731 | A1 | * | 4/2009 | Sanada | ................... | A61B 5/418 382/132 |
| 2012/0095326 | A1 | * | 4/2012 | Miyazaki | ............. | A61B 5/0263 600/413 |
| 2012/0212222 | A1 | * | 8/2012 | Subramanian | ..... | G01R 33/5635 324/309 |
| 2013/0257429 | A1 | * | 10/2013 | Edelman | ............ | G01R 33/5635 324/309 |

(Continued)

FOREIGN PATENT DOCUMENTS

JP 5093727 B2 12/2012

*Primary Examiner* — Carol Wang
(74) *Attorney, Agent, or Firm* — Cantor Colburn LLP

(57) ABSTRACT

A dynamic image analysis apparatus includes a hardware processor that acquires an X-ray dynamic image including continuous frame images acquired by continuously capturing a living body having a heartbeat in time series; performs logarithmic conversion for a pixel value of the acquired X-ray dynamic image to create a logarithmically converted image; sets, as a reference frame image, one frame image based on a heartbeat phase in at least one of the X-ray dynamic image and the logarithmically converted image; calculates (i) a difference or ratio between the X-ray dynamic image as the reference frame image and the X-ray dynamic image as a comparative frame image which is another frame image or (ii) a difference or ratio between the logarithmically converted image as the reference frame image and the logarithmically converted image as the comparative frame image; and generates a blood flow analysis image.

11 Claims, 17 Drawing Sheets

(56) References Cited

U.S. PATENT DOCUMENTS

2013/0281846 A1\* 10/2013 Yoshiara .................. A61B 8/06
600/431
2016/0120491 A1\* 5/2016 Shimamura ............ A61B 6/463
348/333.05
2017/0325770 A1\* 11/2017 Edic ....................... A61B 6/503

\* cited by examiner

|  | $\mu$ [cm²/g] | $\rho$ [g/cm³] |
|---|---|---|
| FAT | 0.2 | 0.9 |
| BONE | 0.3 | 1 |
| BLOOD VESSEL (BLOOD) | 0.2 | 1.1 |
| LUNG | 0.2 | 0.2 |

| DIFFERENCE VALUE | R, G, AND B VALUES |
|---|---|
| -1000 | 255,0,0 |
| -500 | 250,0,0 |
| -100 | 50,0,0 |
| 0 | 0,0,0 |
| 100 | 0,50,0 |
| 500 | 0,250,0 |
| 1000 | 0,255,0 |

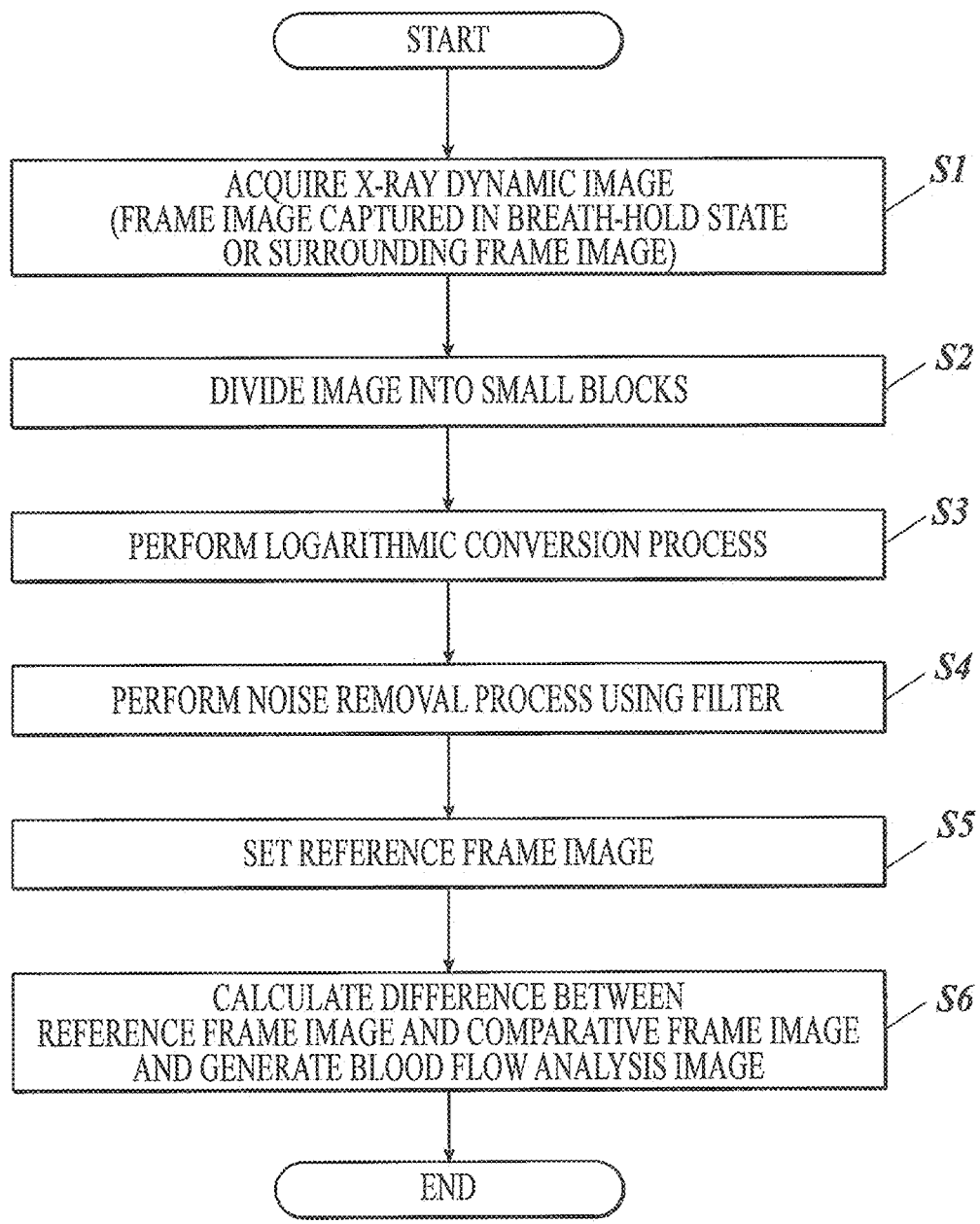

DYNAMIC IMAGE ANALYSIS APPARATUS, DYNAMIC IMAGE ANALYSIS METHOD, AND RECORDING MEDIUM

CROSS REFERENCE TO RELATED APPLICATION

The present application claims priority under 35 U.S.C. § 119 to Japanese Patent Application No. 2018-138096, filed on Jul. 24, 2018, the entire content of which is incorporated herein by reference.

BACKGROUND

1. Technological Field

The present invention relates to a dynamic image analysis apparatus, a dynamic image analysis method, and a recording medium.

2. Description of the Related Art

In a case in which a blood flow in the lungs or the heart is blocked due to, for example, pulmonary embolism or a heart disease, the blocking of the blood flow causes serious symptoms related to life. Therefore, in the related art, for example, a blood flow in the lungs has been analyzed by a lung perfusion scintigraphic examination or a lung angiographic examination.

However, in the lung perfusion scintigraphic examination and the lung angiographic examination, the degree of invasion to the subject is large and an examination apparatus is expensive. Therefore, it is not easy to receive the examinations in any medical institution.

In order to solve the problems, JP 5093727 B2 discloses a method that examines pulmonary embolism or a heart disease causing abnormality in a blood flow, such as a pulmonary blood flow or a cardiac blood flow, using chest X-ray dynamic images which have been continuously captured.

Specifically, among a plurality of captured X-ray images, a frame image corresponding to the R wave in an electrocardiogram is used as a reference frame and the difference between the pixel values (density values) of the reference frame and other frame images is calculated to create a difference image. Then, a temporal change in the density value is recognized and a lung blood flow dynamic image in which the aspect of a lung blood flow is visualized is created.

JP 5093727 B2 focuses on the fact that, in a case in which blood flows from the heart to the lungs in the ventricular systole of the heart and a pulmonary blood flow increases, X-ray transmittance is reduced by the presence of the pulmonary blood flow and the pixel value of the lung field in the chest X-ray dynamic image increases.

Then, assuming that a pixel value is P and an X-ray dose detected by an X-ray detector (an incident dose to the X-ray detector) is N, the relationship of "P∝1/log N" is established.

However, in a case in which the X-ray images of, for example, the lungs are actually captured, X-rays are transmitted through the lung field and various structures, such as surrounding bones and fat, and are acquired as pixel values.

Therefore, in a case in which a blood flow distribution in the lung field is recognized using a value that depends on the amount of X-rays transmitted through the lung field (in the above-mentioned example, a pixel value corresponding to this) as in JP 5093727 B2, various types of noise are mixed. As a result, a correct value is not necessarily obtained.

This is a big problem, particularly, in a case in which a small change in pixel value is recognized as in a case in which a temporal change in blood flow volume caused by the beating of the heart is seen.

SUMMARY

The invention has been made in view of the above-mentioned problems and an object of the invention is to provide a dynamic image analysis apparatus, a dynamic image analysis method, and a recording medium that can obtain a blood flow analysis image using a relatively simple method which analyzes a dynamic image and reduces a burden on a subject.

To achieve at least one of the abovementioned objects, according to an aspect of the present invention, a dynamic image analysis apparatus includes a hardware processor that:

acquires an X-ray dynamic image including continuous frame images acquired by continuously capturing a living body having a heartbeat in time series;

performs logarithmic conversion for a pixel value of the acquired X-ray dynamic image to create a logarithmically converted image;

sets, as a reference frame image, one frame image based on a heartbeat phase in at least one of the X-ray dynamic image and the logarithmically converted image;

calculates (i) a difference or ratio between the X-ray dynamic image as the reference frame image and the X-ray dynamic image as a comparative frame image which is another frame image or (ii) a difference or ratio between the logarithmically converted image as the reference frame image and the logarithmically converted image as the comparative frame image; and generates a blood flow analysis image based on the difference or the ratio.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 18 is a flowchart illustrating a process performed by the analysis apparatus according to this embodiment.

DETAILED DESCRIPTION OF THE PREFERRED EMBODIMENTS

Figure 1:
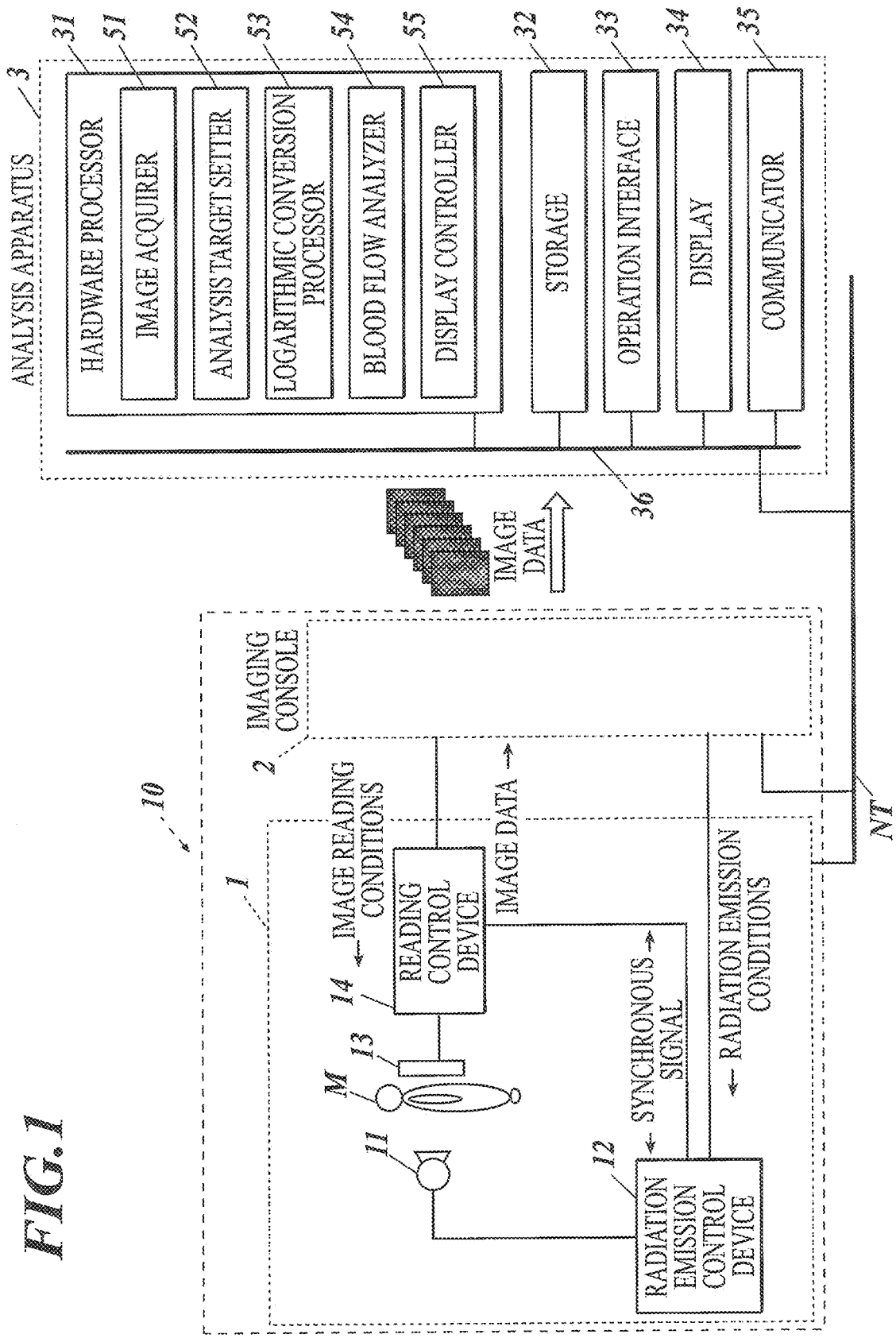
FIG. 1 is a diagram illustrating an analysis system including an analysis apparatus according to an embodiment.

Hereinafter, an embodiment of a dynamic image analysis apparatus (simply referred to as an "analysis apparatus" in the drawings and the following description) according to the invention will be described with reference to the drawings.

In the following embodiments, various technically preferable limitations are imposed in order to carry out the invention. However, the technical scope of the invention is not limited to the following embodiments and illustrated examples.

Positioning of Analysis Apparatus

The analysis apparatus according to this embodiment receives an X-ray dynamic image (hereinafter, simply referred to as a "dynamic image") from an imaging system and displays the received dynamic image or the analysis result of the dynamic image.

First, as a premise, the relationship between the imaging system and the analysis apparatus assumed in the embodiment will be described with reference to FIG. 1.

An imaging system 10 includes an imaging apparatus 1 that can capture a dynamic image and an imaging console 2 that controls the imaging apparatus 1. The imaging apparatus 1 is connected to a communication network NT, such as a local area network (LAN), through the imaging console 2.

An analysis apparatus 3 according to this embodiment is connected to the imaging system 10 through the communication network NT and the dynamic image acquired by the imaging apparatus 1 is transmitted to the analysis apparatus 3 through the imaging console 2.

FIG. 1 illustrates an example in which one imaging apparatus 1 and one imaging console 2 that controls the imaging apparatus 1 are provided. However, the number of imaging apparatuses 1 and the number of imaging consoles 2 for controlling the imaging apparatuses 1 are not limited to one and a plurality of imaging apparatuses 1 and a plurality of imaging consoles 2 may be provided.

In this embodiment, the analysis apparatus 3 which is a dynamic image analysis apparatus may be a diagnosis console that generates, for example, an image for diagnosis (a moving image or the analysis result of the moving image) and displays the image or may be an apparatus other than the diagnosis console.

The imaging system 10 or the analysis apparatus 3 is based on a Digital Image and Communications in Medicine (DICOM) standard and the communication between the apparatuses is performed according to the DICOM standard.

The analysis apparatus 3 or the imaging apparatus 1 does not need to be always connected to the communication network NT.

Configuration of Imaging Apparatus 1

As described above, the imaging apparatus 1 can capture a dynamic image.

The "dynamic image" is obtained by continuously capturing the images of a living body having a heartbeat that is an object in time series and acquiring a plurality of frames of radiographic images as a moving image.

In this embodiment, the capture of the "dynamic image" means dynamic imaging that repeatedly irradiates an object M with pulsed radiation, such as pulsed X-rays, at a predetermined time interval (pulse irradiation) or continuously irradiates the object M at a low dose without interruption (continuous irradiation) to acquire a plurality of images indicating the dynamic state of the object. That is, the "dynamic image" in this embodiment means a plurality of series of images indicating the dynamic state of the object obtained by the above-mentioned imaging operation. Further, each of the plurality of images forming the dynamic image is referred to as a frame image.

In this embodiment, the image of a human body which is the object and a dynamic structure included in the human body is captured as the "dynamic image". Examples of the dynamic structure captured by the imaging apparatus 1 include the lung field, the diaphragm, and the heart. In addition, the dynamic structure in the living body is not limited thereto.

In this embodiment, for example, as illustrated in FIG. 1, the imaging apparatus 1 is a radiography apparatus including a radiation source 11, a radiation emission control device 12, a radiation detector 13, and a reading control device 14.

The radiation emission control device 12 and the radiation detector 13 of the imaging apparatus 1 are connected to the imaging console 2 and the radiation emission control device 12 controls the radiation source 11 to perform radiography on the basis of radiation emission conditions input from the imaging console 2, which will be described below. The radiation detector 13 controls a switch of each pixel to read an electric signal accumulated in each pixel on the basis of image reading conditions input from the imaging console 2, acquires image data, and outputs the acquired image data of the frame image to the imaging console 2.

The radiation source 11 is provided at a position where the radiation source 11 faces the radiation detector 13 with the object M (subject) interposed there between and irradiates the object M with radiation (X-ray) under the control of the radiation emission control device 12.

The radiation emission control device 12 is connected to the imaging console 2 and controls the radiation source 11 on the basis of the radiation emission conditions input from the imaging console 2 such that radiography is performed. The radiation emission conditions input from the imaging console 2 include, for example, a pulse rate, a pulse width, a pulse interval, the number of frames captured by each imaging operation, the value of an X-ray tube current, the value of an X-ray tube voltage, and the type of additional filter. The pulse rate is the number of times radiation is emitted per second and is equal to a frame rate which will be described below. The pulse width is the irradiation time per irradiation operation. The pulse interval is the time from the start of one irradiation operation to the start of the next irradiation operation and is identical to a frame interval which will be described below.

The radiation detector 13 is provided at a position where the radiation detector 13 faces the radiation source 11 with the object M interposed therebetween.

The radiation detector 13 includes a semiconductor image sensor such as a flat panel detector (FPD). The FPD includes, for example, a glass substrate and has a plurality of detection elements (pixels) that are arranged in a matrix at predetermined positions on the substrate, detect the radiation which has been emitted from the radiation source 11 and then passed through at least the object M according to the intensity of the radiation, convert the detected radiation into an electric signal, and accumulate the electric signal. Each pixel includes a switch such as a thin film transistor (TFT).

The reading control device 14 is connected to the imaging console 2. The reading control device 14 controls the switch of each pixel of the radiation detector 13 on the basis of the image reading conditions input from the imaging console 2 such that the reading of the electric signal accumulated in each pixel is switched and reads the electric signal accumulated in the radiation detector 13 to acquire image data. The image data is a frame image. A pixel signal value (hereinafter, also simply referred to as a "signal value") of the frame image indicates a density value. Then, the reading control device 14 outputs the acquired frame image to the imaging console 2. The image reading conditions include, for example, a frame rate, a frame interval, a pixel size, and an image size (matrix size). The frame rate is the number of frame images acquired per second and is identical to the pulse rate. The frame interval is the time from the start of an operation of acquiring a first frame image to the start of an operation of acquiring the next frame image and is identical to the pulse interval.

The radiation emission control device 12 and the reading control device 14 are connected to each other and exchange a synchronous signal therebetween to synchronize a radiation emission operation with an image reading operation.

Configuration of Imaging Console 2

The imaging console 2 outputs the radiation emission conditions or the image reading conditions to the imaging apparatus 1 to control a radiography operation and a radiographic image reading operation of the imaging apparatus 1 and displays the dynamic image acquired by the imaging apparatus 1 such that a radiology operator, such as a radiology technician, can check positioning or whether the dynamic image is suitable for diagnosis.

The imaging console 2 includes, for example, a hardware processor, a storage, and an operation interface which are not illustrated in the drawings and performs various processes including an imaging control process corresponding to the imaging conditions (the radiation emission conditions and the image reading conditions) according to various processing programs.

In this embodiment, it is preferable to control the movement of the body of the object M at the time of imaging as much as possible in order to prevent the generation of artifacts by, for example, the shaking of the body of the subject that is the object M.

In a case in which a blood flow in the heart or the lung is analyzed using the dynamic image (X-ray dynamic image), a very small change in density is measured. Therefore, a change in the density of the structure to be analyzed and the influence of the movement of various structures are mixed by even a slight movement of the structure at the time of imaging. As a result, it is difficult to correctly recognize a change in the density of the structure to be analyzed and to correctly recognize a biological function of the structure.

For example, even in a case in which the shaking of the body of the object M does not occur, noise is included in the captured image only by the expansion and contraction of the periphery of the lung field caused by breathing, which prevents accurate image analysis.

Therefore, it is preferable that the imaging console 2 sets the imaging conditions such that imaging is performed while keeping the object M in a breath-hold state for a predetermined period of time (for example, about 6 seconds). As such, in a case in which imaging is performed in the breath-hold state, it is possible to reduce noise included in the dynamic image to be analyzed by the analysis apparatus 3 as much as possible.

In practice, it is desirable that the radiology technician performs imaging on the basis of the set imaging conditions while checking the state of the object.

For example, in a case in which the respiratory volume of the object M is small, imaging may be performed during quiet breathing. During breathing, the radiology technician may instruct the object M to hold the breath and may perform imaging after the object M is in a breath-hold state. Some patients have difficulty in quiet breathing or holding their breath. Therefore, imaging may be performed in a state in which the patient breathes a large amount of air, such as a state in which the patient breathes deeply.

It may be difficult or impossible to visibly check whether or not the patient holds the breath. Therefore, it may be detected whether or not the breath holding is properly performed using, for example, a camera image or a pressure sensor and the detection result may be displayed on, for example, a display (not illustrated).

It is desirable to store movement information obtained by, for example, a camera image or a pressure sensor at the time of imaging (for example, information indicating whether the body has moved due to the shaking of the body or breathing, or the amount of movement indicating how much the body moves in a case in which the body has moved) or the amount of movement calculated from the movement information so as to be associated with the dynamic image in order to prevent an imaging error or to determine the optimum frame to be analyzed. Further, a frame image with a small amount of movement may be stored as the range of frame images suitable for analysis in the analysis apparatus 3 (which is referred to as an "analysis target frame range"; see FIG. 3B) so as to be associated with the dynamic image. Conversely, the movement information of each frame image may be extracted from the captured dynamic images.

For example, the period of the frame image captured in the breath-hold state on an imaging protocol may be predetermined in order to omit calculation for setting the analysis target frame range. Then, an optimal analysis target frame range may be calculated from the predetermined period of the frame images captured in the breath-hold state.

Since movement caused by the body motion or breathing of the patient causes an artifact in the analysis result as described above, it is desirable to set the analysis target frame range to a range excluding a frame image in which movement caused by the body motion or breathing of the object M occurs (or is likely to occur) in order to improve the analysis accuracy of the analysis apparatus 3.

In this embodiment, an example in which an analysis target setter 52 of the analysis apparatus 3 which will be described below calculates the amount of movement is described. However, the imaging console 2 may calculate the amount of movement. In this case, the amount of movement is calculated by the same method as that in the analysis target setter 52.

Configuration of Analysis Apparatus 3

The analysis apparatus 3 is a dynamic image analysis apparatus acquires the dynamic image (X-ray dynamic image) captured by the imaging apparatus 1 and generates a blood flow analysis image.

In this embodiment, specifically, the analysis apparatus 3 sets the frame image range (analysis target frame range) suitable for blood flow analysis, uses any frame image in the frame image range as a reference frame image, and compares other frames in the analysis target frame range with the reference frame image to perform blood flow analysis.

Hereinafter, for example, each component of the analysis apparatus 3 according to this embodiment and a specific blood flow analysis method will be described in detail.

The dynamic image, the X-ray dynamic image, the frame image, and a logarithmically converted image in this specification include an image of the entire region of each image and an image obtained by extracting a partial region of each image.

As illustrated in FIG. 1, the analysis apparatus 3 includes a hardware processor 31, a storage 32, an operation interface 33, a display 34, and a communicator 35 which are connected to each other by a bus 36.

In this embodiment, the analysis apparatus 3 is a diagnosis console which supports the doctor's diagnosis and is an image processing apparatus that receives the dynamic image from the imaging console 2, analyzes the received dynamic image, performs image processing, displays the analysis result on the display 34 (which will be described below) of the analysis apparatus 3 or an external display device (not illustrated), or performs analysis again.

FIG. 1 illustrates a case in which the analysis apparatus 3 which is the diagnosis console and the imaging console 2 are separate apparatuses. However, the configuration of the system is not limited thereto.

For example, the analysis apparatus 3 as the diagnosis console may also have the functions of the imaging console 2, and the analysis apparatus 3 and the imaging apparatus 1 may be connected to each other by the communication network NT.

The analysis apparatus 3 may be provided separately from the diagnosis console.

The operation interface 33 of the analysis apparatus 3 includes a keyboard including, for example, cursor keys, numeric input keys, and various function keys and a pointing device, such as a mouse, and outputs an instruction signal input by a key operation for the keyboard or a mouse operation of the user to the hardware processor 31. In addition, the operation interface 33 may include a touch panel provided in a display screen of the display 34. In this case, the operation interface 33 outputs an instruction signal input through the touch panel to the hardware processor 31.

The display 34 is a monitor, such as a liquid crystal display (LCD) or a cathode ray tube (CRT), and displays various kinds of information in response to a display signal input from the hardware processor 31.

The display 34 may have the function of a display device for displaying the analysis result and the display device for displaying the analysis result may be provided separately from the analysis apparatus 3.

The communicator 35 includes, for example, a LAN adapter, a modem, or a TA and controls the transmission and reception of data to and from each device connected to the communication network NT.

The storage 32 is, for example, a non-volatile semiconductor memory or a hard disk drive. The storage 32 stores various programs including a program for executing a diagnosis support process in the hardware processor 31, parameters required for the execution of processes by the programs, or data such as processing results. The various programs are stored in the form of readable program codes and the hardware processor 31 sequentially performs operations corresponding to the program codes.

The dynamic image captured in the past is stored in the storage 32 so as to be associated with, for example, an identification ID, patient information (object attribute information, for example, a patient ID and the name, height, weight, age, and sex of a patient/object), and examination information, for example, an examination ID, an examination date, and a part to be examined (here, the chest). In addition, list information including patient information or examination information related to each dynamic image started to be received from the imaging console 2 and status (for example, a progress state, such as a state in which information is being received, a state in which an analysis process is being performed, and a state in which analysis has ended) is stored in the storage 32.

In a case in which the analysis apparatus 3 transmits and receives information to and from, for example, the imaging system 10 according to DICOM, the patient information as described above is transmitted together with the data of the dynamic image and is stored in the storage 32 so as to be associated with the dynamic image.

The analysis result (for example, a blood flow analysis image) is stored in the storage 32 so as to be associated with the dynamic image.

The hardware processor 31 is a computer of the analysis apparatus 3 which includes a central processing unit (CPU) and a random access memory (RAM). The CPU of the hardware processor 31 reads the system program or various processing programs stored in the storage 32 in response to the operation of the operation interface 33, expands the program in the RAM, and performs various processes according to the expanded program to intensively control each component of the analysis apparatus 3.

In this embodiment, the hardware processor 31 receives the dynamic image (X-ray dynamic image) captured by the imaging system 10 and sets any one of a plurality of frame images forming the dynamic image as the reference frame image.

The analysis apparatus 3 can calculate the difference or ratio between the reference frame image and other frame images to analyze a cardiac blood flow into and out of the heart and a pulmonary blood flow into or out of the lung (lung field), generate a blood flow analysis image, visualize the blood flow analysis image, and provide the blood flow analysis image to, for example, the doctor.

Figure 2:
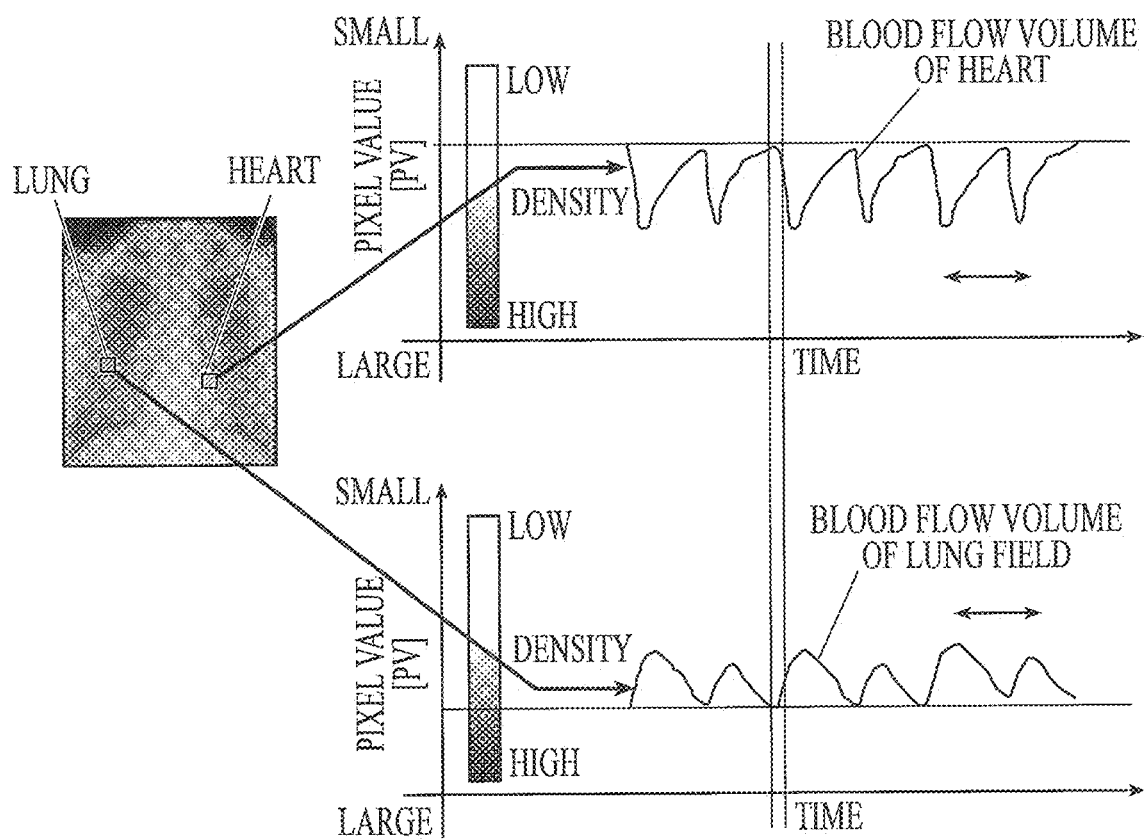
FIG. 2 is a diagram illustrating a change in blood flow volume in the heart and the lung field.

FIG. 2 illustrates a graph indicating an increase or decrease in the blood flow volume of the heart on the upper side and a graph indicating an increase or decrease in the blood flow volume of the lung field on the lower side. In each graph of FIG. 2, the vertical axis indicates a pixel value and the degree of density.

In a case in which blood flows into an organ, a blood flow prevents the transmission of X-rays. Therefore, the amount of X-rays transmitted in the X-ray image is reduced and a pixel value is reduced. As a result, the blood vessel appears white (that is, at low density) in the X-ray image.

From the relationship between a cardiac blood flow into and out of the heart and a pulmonary blood flow into and out of the lung field, as illustrated in FIG. 2, in a case in which the heart is in ventricular diastole and a large amount of blood flows into the heart, X-ray transmission is blocked in the heart part. Therefore, a pixel value is small and the heart part appears relatively white (at low density) in the X-ray image. In contrast, at this timing, a small amount of blood flows into the lung field and the amount of X-rays transmitted in the lung field part is large. As a result, a pixel value is large in the X-ray image and the lung field appears relatively dark (at high density) in the X-ray image.

Conversely, in a case in which the heart is in ventricular systole and blood flows out of the heart, the amount of X-rays transmitted through the heart part is large. Therefore, a pixel value is large in the X-ray image and the heart part appears relatively dark (at high density) in the X-ray image. In contrast, at this timing, a large amount of blood flows from the heart into the lung field and X-ray transmission through the lung field is blocked. As a result, a pixel value is small in the X-ray image and the lung field appears relatively white (at low density) in the X-ray image.

As such, the beating of the heart and an increase or decrease in the blood flow in the lung field have a relationship therebetween and are repeated.

The relationship between the beating of the heart and the increase or decrease in the blood flow in the lung field coincides with the reliable result of the blood flow scintigraphic examination performed in the related art.

As illustrated in FIG. 1 which is a functional diagram, the hardware processor 31 according to this embodiment includes an image acquirer 51, the analysis target setter 52, a logarithmic conversion processor 53, a blood flow analyzer 54, and a display controller 55.

The hardware processor 31 functions as, for example, the image acquirer 51, the analysis target setter 52, the logarithmic conversion processor 53, the blood flow analyzer 54, and the display controller 55 in cooperation with a program.

The image acquirer 51 acquires a dynamic image (X-ray dynamic image) including a plurality of continuous frame images acquired by continuously capturing a living body having a heartbeat (in this embodiment, for example, the chest including the heart and the lung field of the object M that is a person) in time series.

Specifically, the image acquirer 51 acquires data of the dynamic image transmitted from, for example, the imaging console 2 to the communicator 35 of the analysis apparatus 3.

As described above, in a case in which the imaging console 2 calculates, for example, the amount of movement caused by the body motion or breathing of the object M (subject), the image acquirer 51 also acquires information, such as the calculation result, through the communicator 35.

The analysis target setter 52 sets, for example, a frame image used to generate a blood flow analysis image among a plurality of continuous frame images acquired by the image acquirer 51.

Specifically, the analysis target setter 52 sets, as the reference frame image, one frame image based on a heartbeat phase in at least one of the dynamic image (X-ray dynamic image) acquired by the image acquirer 51 and the logarithmically converted image (which will be described below) obtained by performing a logarithmic conversion process for the dynamic image.

The heartbeat phase is the timing of the beating of the heart (heartbeat) within one cycle.

For the heart, one heartbeat cycle is formed by a set of ventricular diastole and ventricular systole. In the ventricular systole, blood is pumped from the heart. In a case in which blood is pumped from the heart, an electric signal which is called an R wave is transmitted to the heart muscle. In a case in which the R wave is transmitted, the heart starts to be contracted in response to the R wave as a trigger and blood is pumped from the heart to the peripheral blood vessel.

The analysis target setter 52 sets, for example, as the reference frame image, one of the frame images captured at any point of time in the heartbeat cycle as described above according to the purpose of blood flow analysis (that is, for example, which blood vessel do you want to observe a blood flow).

It is preferable that the reference frame image is any frame image in the analysis target frame range.

In a case in which a dynamic image including, for example, movement caused by a body motion caused by the shaking of the body of the object M or breathing is used for blood flow analysis, components other than a change in blood flow volume are included, which makes it difficult to correctly recognize the change in blood flow volume.

Therefore, in this embodiment, the analysis target setter 52 detects movement (that is, movement caused by the body movement or breathing of the object M) that becomes a blood flow artifact from the frame image, sets a range in which frame images without movement that becomes a blood flow artifact (or in which the amount of movement is equal to or less than an allowable limit) among a plurality of frame images are continuous as the analysis target frame range, and selects the reference frame image and a comparative frame image to be compared with the reference frame image in the range.

For example, in a case in which a blood flow analysis target is a pulmonary blood flow, it is necessary to perform analysis using frame images within the range in which the state in which the lung field does not move is maintained.

Therefore, for example, the movement of the lung field, particularly, the movement of the periphery of the lung field is detected to measure and recognize the amount of movement with high accuracy. In a case in which the amount of movement is equal to or greater than a predetermined value, the frame image captured in a state in which the movement occurs may not be used for blood flow analysis. Various methods can be used to detect the amount of movement of the periphery of the lung field. For example, it is considered that a method, such as template matching, is used to perform measurement.

As a method for measuring the amount of movement, for example, the amount of movement of the periphery of the outer thorax or the periphery of the diaphragm which is a part other than the part (for example, the heart) forming the periphery of the lung field may be measured.

Even in a case in which the movement of structures other than the lung filed, such as the scapula, the breast, the ribs, and the clavicle that overlap the lung field, is large, the movement is likely to be an artifact due to a large change in the signal value. Therefore, the movement of structures other than the lung field may also be detected. In a case in which the amount of movement equal to or greater than a predetermined value is detected, it may be determined that the frame image is captured in a state in which movement occurs and the frame image may not be used for blood flow analysis.

The difference between the frame images may be calculated to create a difference image and the number of pixels whose value has been changed by a threshold value or more in the area in which a target structure whose movement amount is desired to be recognized is present may be calculated. Then, the amount of movement may be detected on the basis of the number of pixels.

For the calculation of the amount of movement, for example, the absolute value of a temporal change in the density value of each pixel of the dynamic image is calculated and the spatial average or median of the absolute value is calculated as the amount of movement in each frame image.

In this case, since movement caused by the beating of the heart which does not affect the analysis is also detected as the amount of movement, it is more desirable to calculate an average or a median for regions except the region of the heart.

For example, in order to detect only movement caused by breathing with high accuracy, it is desirable to detect the position of the diaphragm and to detect the amount of movement of the diaphragm. The amount of movement of the diaphragm can be calculated by the absolute value of a temporal change (differentiation) in the position of the diaphragm.

The amounts of movement may be combined from a plurality of structures and it may be determined whether to use the frame image captured in the movement situation for blood flow analysis. In this case, the movement of each structure may be multiplied by a coefficient for the degree of influence on a blood flow artifact to comprehensively calculate the amount of movement.

In this case, for example, a threshold value indicating whether a frame image can be used for blood flow analysis is set and it is determined that the frame image is not used for blood flow analysis in a case in which movement greater than the threshold value is included in the frame image.

Figure 3A:
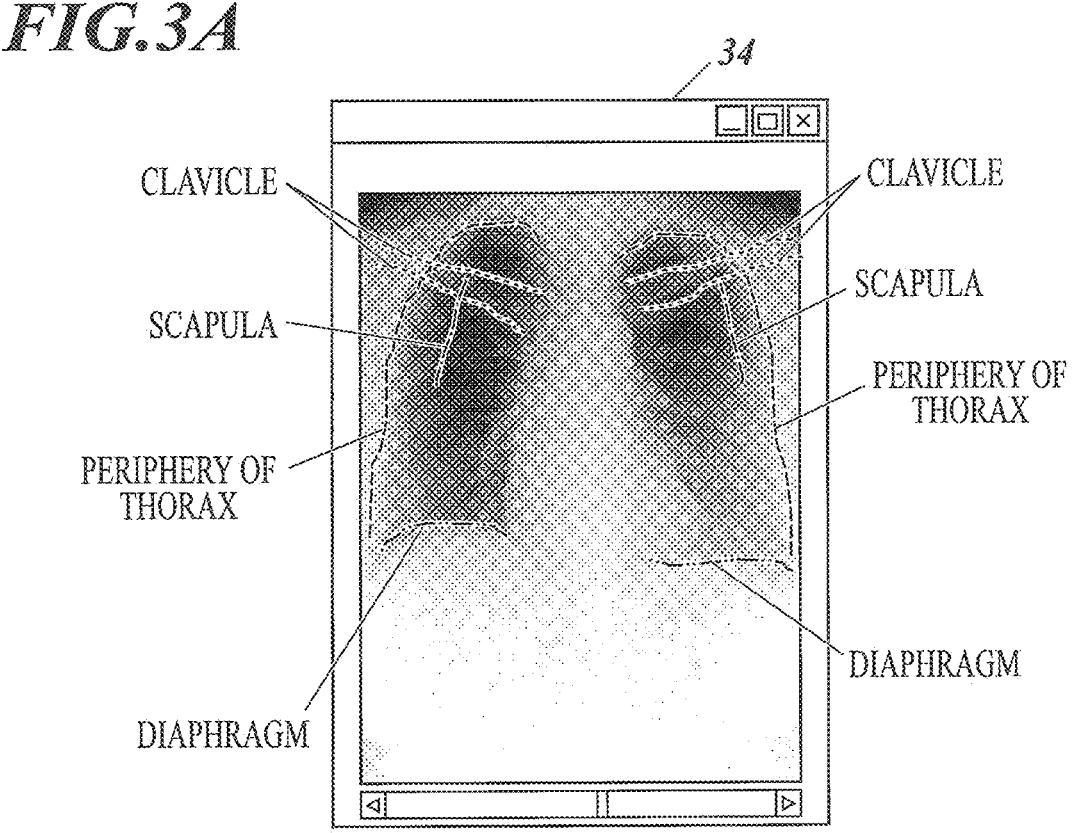
FIG. 3A is a diagram illustrating an example of a chest X-ray image of the human body.

For example, it is assumed that the amounts of movement of structures, such as the diaphragm, the thorax (the periphery of the thorax), the clavicle, and the scapula illustrated in FIG. 3A, are combined with each other, the amounts of movement of each structure (the amount of movement between two frame images) are as follows:

the amount of movement of the diaphragm is 5 mm;

the amount of movement of the thorax (the periphery of the thorax) is 0.5 mm;

the amount of movement of the clavicle is 1 mm; and the amount of movement of the scapula is 0 mm.

Coefficients for the degree of influence of each structure on a blood flow artifact are as follows:

a coefficient for the degree of influence of the diaphragm is 0.3;

a coefficient for the degree of influence of the thorax (the periphery of the thorax) is 1;

a coefficient for the degree of influence of the clavicle is 0.1; and a coefficient for the degree of influence of the scapula is 0.7.

In this case, if the amounts of movement are multiplied by the coefficients, a value of 1.5 is obtained for the diaphragm, a value of 0.5 is obtained for the thorax (the periphery of the thorax), a value of 0.1 is obtained for the clavicle, and a value of 0 is obtained for the scapula. Then, the degree of blood flow artifact obtained by integrating all of the values is 2.1.

Figure 3B:
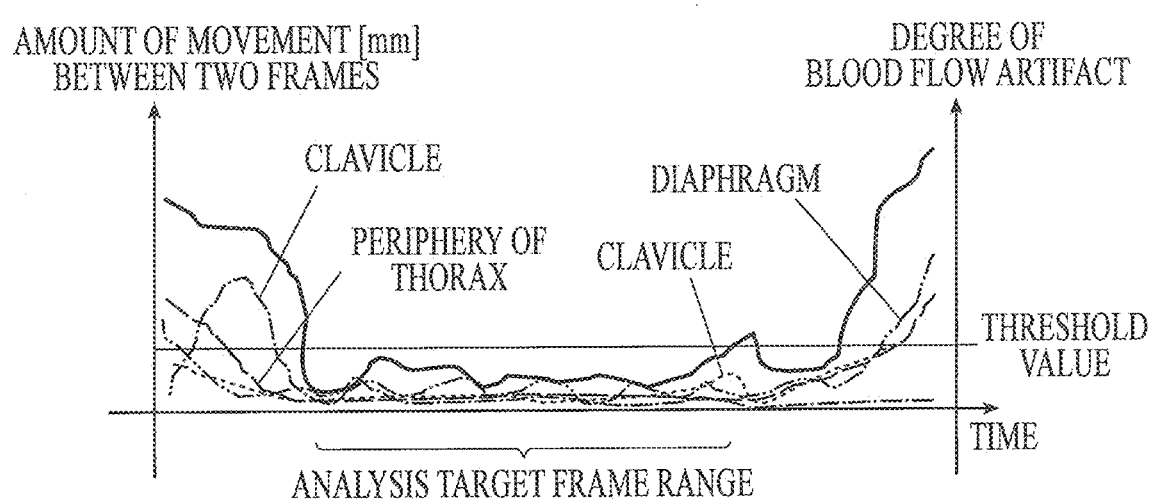
FIG. 3B is a graph illustrating an example of the amount of movement of each structure in FIG. 3A.

FIG. 3B is a graph obtained by calculating the degree of blood flow artifact for each of a plurality of continuous frame images. In the graph illustrated in FIG. 3B, the diaphragm is represented by a two-dot chain line, the thorax (the periphery of the thorax) is represented by a dashed line, the clavicle is represented by a dotted line, the scapula is represented by a one-dot chain line, and the degree of blood flow artifact is represented by a solid line in accordance with FIG. 3A.

FIG. 3B illustrates an example in which a frame image having the degree of blood flow artifact greater than a predetermined threshold value is not used for blood flow analysis and the range of continuous frame images having the degree of blood flow artifact equal to or less than the predetermined threshold value is the range of frame images to be subjected to blood flow analysis (this is referred to as an analysis target frame range).

As a method for setting the analysis target frame range, for example, a predetermined number of frame images (two or more continuous frame images) between which the amount of movement is equal to or greater than a threshold value are selected as defective frame images and a frame range with the maximum length which does not include the defective frame images is set as the analysis target frame range.

The amount of movement between a predetermined number of frame images (two or more continuous frame images) may be calculated in advance and a frame range in which the sum of the amounts of movement is the minimum in the analysis target frame range may be selected as the analysis target frame range.

As such, the frame image including movement which becomes a blood flow artifact is excluded from the frame range to be subjected to blood flow analysis as much as possible. Therefore, it is possible to exclude a blood flow artifact from the blood flow analysis image.

As a result, it is possible to obtain a blood flow analysis image from which components other than a change in blood flow volume have been removed, to correctly recognize the change in blood flow volume, and to perform an appropriate diagnosis.

That is, a blood flow analysis image is generated by the frame image captured in a state in which the object M does not move and the cessation of breathing (breath-hold) is maintained. Therefore, it is possible to satisfy the assumption that components other than a change in blood flow volume do not change over time and to correctly recognize a change in material blood flow volume.

In a case in which the imaging console 2 sets the analysis target frame range or in a case in which the imaging console 2 calculates the amount of movement of the analysis target or other structures if the analysis target or other structures move and the image acquirer 51 acquires the information, the analysis apparatus 3 may set the analysis target with reference to the information.

As such, even in a case in which a frame image including movement that becomes a blood flow artifact is excluded from the frame range to be subjected to blood flow analysis as much as possible, movement that becomes a blood flow artifact and is equal to or greater than a predetermined threshold value may be included in the analysis target frame range as a result.

In this case, in addition to the display of the blood flow analysis image (the result of the blood flow analysis), for example, a warning indicating that there is movement that becomes a blood flow artifact is preferably displayed to warn the user.

The quantitative value of the movement that becomes a blood flow artifact in the analysis target frame range may be displayed such that the user can objectively determine the degree of blood flow artifact.

It is desirable to set the analysis target frame range, considering noise control by a filtering process which will be described below.

For convenience, for example, it is desirable to select, as the analysis target frame range, a range in which the period for which the frame images having the amount of movement of the diaphragm equal to or less than a threshold value are continuous is the longest.

In a case in which a predetermined number of frames from the beginning and the end of the analysis target frame range are not capable of being analyzed by the filter process, for example, in a case in which frames corresponding to the first two seconds and the last two seconds are not capable of being analyzed, the length of the analysis target frame range may be set in advance to a range of one heartbeat +the first two seconds +the last two seconds and a frame range in which, for example, the maximum value, average, or median of the amounts of movement is the smallest in the set range may be selected as the analysis target frame range.

A frame range in which the number of times ventricular end-diastole appears is large in the range of the middle of a period except the first two seconds and the last two seconds may be selected as the analysis target frame range.

For example, in a case in which the ventricular end-diastole appears twice, it is possible to create a moving image of a blood flow in which the aspect of a pulmonary blood flow corresponding to one heartbeat is continuous. For example, in a case in which the ventricular end-diastole appears three times, a continuous moving image corresponding to two heartbeats is obtained. For example, in a case in which the ventricular end-diastole appears only once, it is difficult to obtain a continuous moving image corresponding to one heartbeat. Therefore, it is preferable to select a frame range in which the ventricular end-diastole appears two or more times.

Next, a method for setting the reference frame image in the analysis target setter 52 according to this embodiment will be described.

In this embodiment, the frame image captured at specific timing may be defined as the reference frame image, or the frame image captured at the most appropriate timing may be set as the reference frame image according to various blood flow states to be analyzed and various blood flow analysis processes may be performed.

As a method for determining which of the frame images captured at any timing is set as the reference frame image in the analysis target setter 52, for example, the following first method is considered.

That is, a frame image corresponding to the ventricular end-diastole of the heart is set as the reference frame image.

Figure 4:
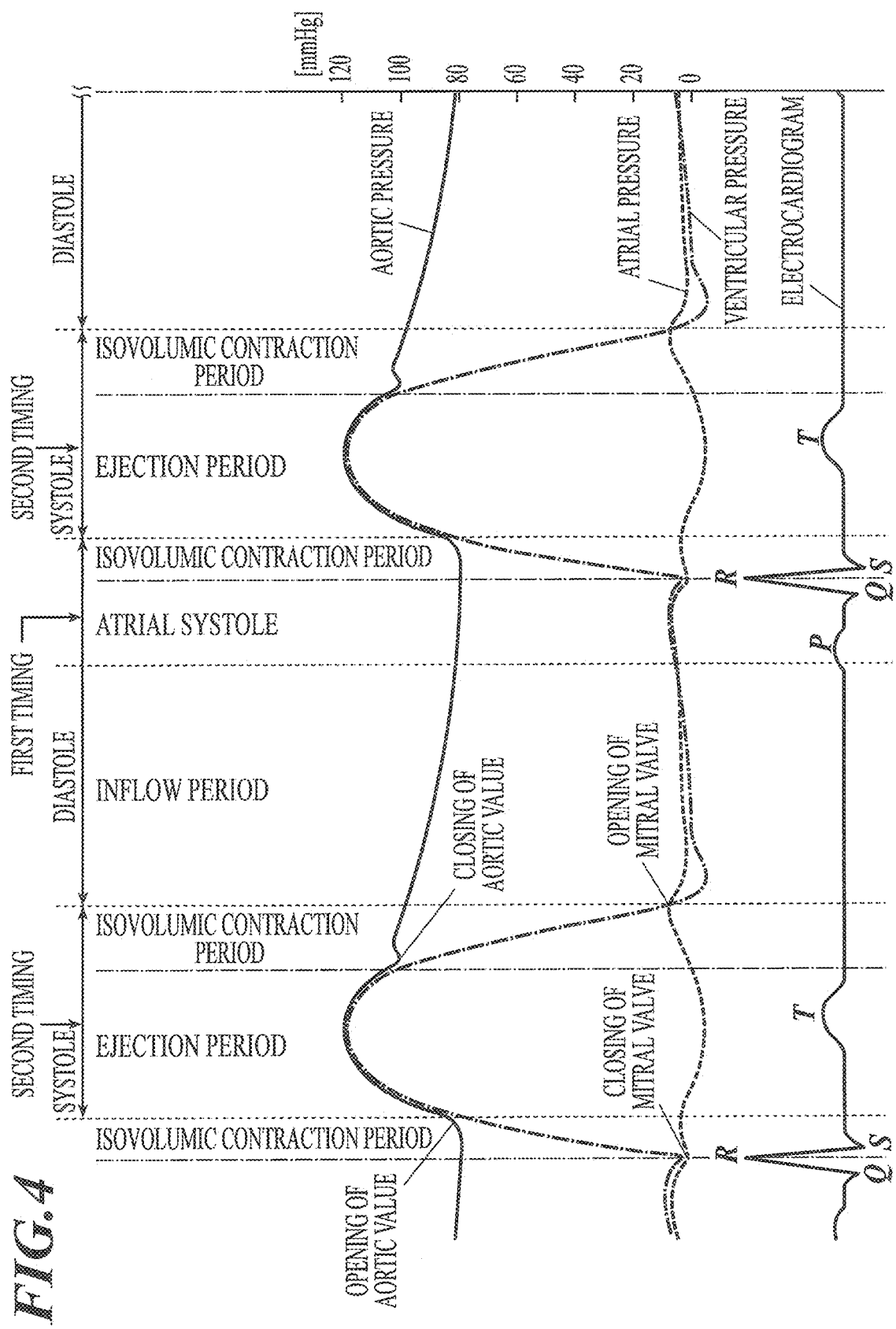
FIG. 4 is a diagram illustrating the cycle of the heartbeat.

FIG. 4 is a graph illustrating the association between a heartbeat phase and an electrocardiogram and a time-series change in each of the heartbeat phase and the electrocardiogram. In FIG. 4, the setting timing of the reference frame image in the first method is illustrated as a first timing.

As illustrated in FIG. 4, the heartbeat phases are mainly classified into ventricular systole and ventricular diastole which are periodically repeated.

For example, in the case of the pulmonary artery, blood is pumped from the left ventricle and the right ventricle has the same movement almost in the same phase. Then, blood is returned from the pulmonary vein to the atrium and the ventricle in diastole (ventricular diastole) and the amount of blood in the ventricle is the largest in the end-diastole (ventricular end-diastole). Immediately after the end-diastole, the aortic valve is opened at the beginning of the systole (ventricular systole) and a large amount of pulmonary blood is pumped from the left ventricle to the pulmonary artery at once by the contraction of the myocardium (an ejection period in systole).

Among them, the first timing selected in the first method is, for example, timing immediately before the ventricle changes from diastole to systole.

In blood flow analysis, since a change in pixel value due to a change in blood volume is very small, there is a problem that the change in pixel value to be analyzed is likely to be buried in various types of noise.

For this reason, according to the first method, a frame image at the timing when the largest amount of blood flows into the heart and the least amount of blood flows to other organs is set as the reference frame image.

Therefore, a subsequent change in blood volume is not buried in noise and can be relatively accurately measured.

There is a slight deviation in the heartbeat phase (that is, the difference between the position where blood arrives earlier and the position where blood arrives later due to the timing of the heartbeat) depending on the position in the lung field. A frame image at the timing immediately before blood is pumped from the heart is set as the reference frame image, which makes it possible to minimize the influence of the deviation.

Blood flow analysis has a problem that it is difficult to measure the value of a correct answer since the analysis target is a living body and it is difficult to verify correctness.

In the case of the first method, since an increment in pulmonary blood flow due to the heartbeat is obtained as an image, the image can be captured as a functional image of the pulmonary blood flow. In addition, since information relatively close to the result of the blood flow scintigraphic examination whose reliability has already been ensured is obtained as an image, there is an advantage that it is easy to verify the correctness of the analysis result.

Figure 5:
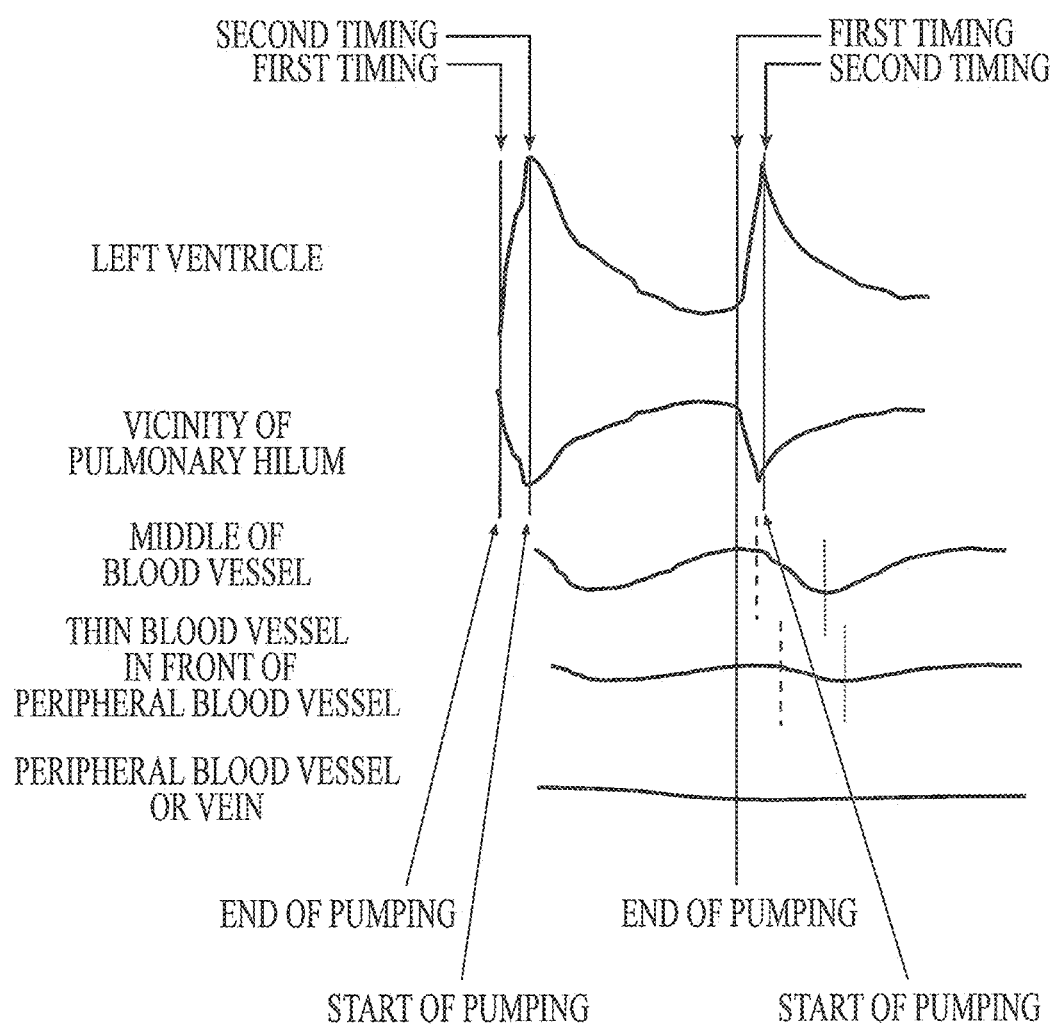
FIG. 5 is a diagram illustrating a change in the pixel value of the main structures in the vicinity of the lung field based on a heartbeat phase.

FIG. 5 is a diagram illustrating the comparison among the phase of the ventricle (the left ventricle in FIG. 5), a phase in the vicinity of the pulmonary hilum, a phase in the middle of the blood vessel, a phase in a thin blood vessel in front of a peripheral blood vessel, and a phase in the peripheral blood vessel or the vein.

A change in the pixel value varies depending on the heartbeat phase. A blood flow arrival start time and a blood flow arrival end time vary depending on the position in the lung field.

As illustrated in FIG. 5, the pixel value varies almost in the same phase in the left ventricle and in the vicinity of the pulmonary hilum. For example, in FIG. 5, the blood pumping start time and the blood pumping end time of the left ventricle of the heart are represented by solid lines. In a case in which a frame image corresponding to the end-diastole of the heart is used as the reference frame image, an ejection end time is the first timing and it can be seen that the phase at blood vessel positions other than the vicinity of the pulmonary hilum is almost the same as that at the blood vessel arrival start time. Therefore, it is desirable that the frame image at the first timing is used as the reference frame image in all pixels in blood analysis.

Next, as the method for setting the reference frame image in the analysis target setter 52, for example, the following second method is considered.

That is, a frame image corresponding to the ventricular systole of the heart after a heartbeat is generated is set as the reference frame image.

In FIG. 4, the timing when the reference frame image is set in the second method is illustrated as a second timing.

As described above, the heart is changed from ventricular diastole to ventricular systole in response to the R wave as a trigger. That is, since the heartbeat is generated after the R wave is detected, the analysis target setter 52 sets a frame image captured at any timing during the period from the detection of the R wave (the peak of the waveform of the R-wave) to the ventricular systole as the reference frame image. Therefore, a frame image corresponding to the second timing can be used as the reference frame image.

For example, the R wave is detected by acquiring an electrocardiogram in parallel to imaging.

In a case in which a frame image corresponding to the ventricular end-diastole of the heart is used as the reference frame image as in the first method, the influence of movement caused by the beating of the heart is large. In this case, density is changed not only by the movement of the heart or the blood vessels, but also by the deformation of the entire lung field. In addition, a change in the blood volume of thick pulmonary blood vessels in the vicinity of the pulmonary hilum is dominant and it is difficult to recognize a change in the blood volume of blood vessels close to a narrow peripheral.

According to the second method, it is possible to observe a change in the blood volume before the blood pumped from the heart reaches peripheral blood vessels. This makes it possible to minimize the influence of movement caused by the beating of the heart and to accurately recognize the distribution of a change in the blood volume of thin blood vessels such as peripheral blood vessels.

As described above, in a case in which the first method that sets a frame image corresponding to the ventricular end-diastole as the reference frame image is used, there are various advantages. However, various advantages that are not capable of being obtained by the first method can be obtained by shifting the setting timing of the reference frame image backward in time.

Therefore, as described above, in this embodiment, the setting of the reference frame image at the first timing according to the first method is not excluded. In addition, it is preferable to calculate a blood flow analysis image using the reference frame image set at, for example, the second timing different from the first timing in the first method, according to the purpose of blood flow analysis.

An X-ray image is a transmission image. Therefore, in a case in which blood flow analysis is performed, the analysis value of the X-ray image (the value of a change in blood volume) is a value obtained by integrating all density changes from a root part (thick blood vessel) to a peripheral part (a thin blood vessel in the peripheral part or a blood vessel in the vicinity of the peripheral part) of the blood vessel. Even in a case in which there is a difference in blood flow volume tendency between the root part and the peripheral part, it is difficult to recognize the difference.

For example, in pulmonary hypertension, it is assumed that the blood flow volume increases in the root part of the blood vessel, and the blood vessel is blocked in the peripheral part or in the vicinity of the peripheral part, resulting in a reduction in the blood flow volume. In a case in which blood flow analysis is performed using the dynamic image, both parts are overlapped and neutralized and a reduction in the blood flow volume in a diseased area in the vicinity of the periphery does not appear in the image. As a result, it is difficult to accuracy determine the disease.

Therefore, as in the second method, the time (timing) when the reference frame image is set is "after" the blood flow arrival start time to the root part (thick blood vessel) of the blood vessel to reduce the influence of an increase or decrease in the blood flow volume in the root part (thick blood vessel) of the blood vessel.

Figure 6D:
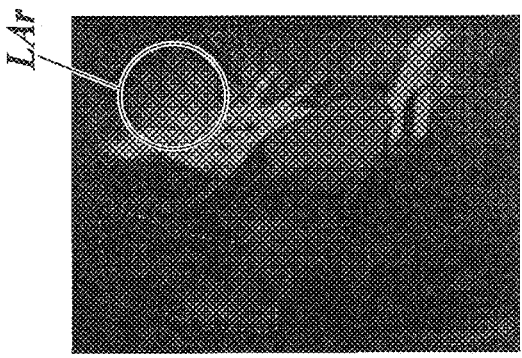
FIG. 6D is a diagram illustrating an example of a blood flow analysis image in a case in which the reference frame image is set at a second timing.
Figure 6C:
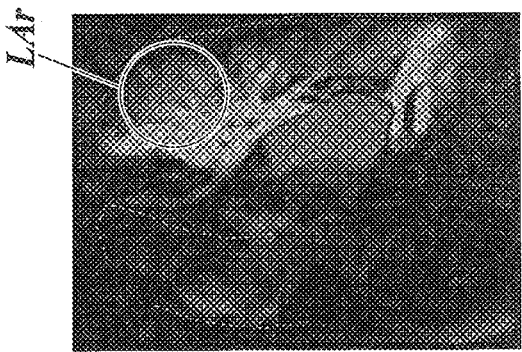
FIG. 6C is a diagram illustrating an example of a blood flow analysis image in a case in which a reference frame image is set at a first timing.
Figure 6B:
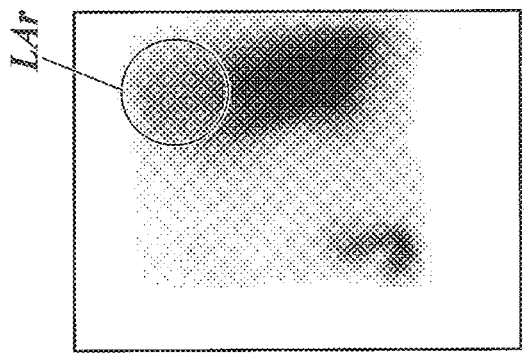
FIG. 6B is a diagram illustrating the result of a blood flow scintigraphic examination on the chest.
Figure 6A:
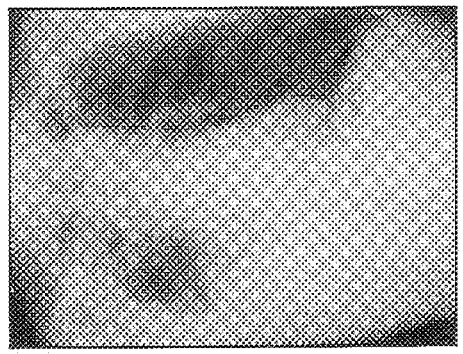
FIG. 6A is a diagram illustrating an example of a chest X-ray image.

FIG. 6A illustrates an example of the X-ray image of the chest.

As illustrated in FIG. 6A, only the X-ray image of the chest is insufficient to observe the state of the blood flow in the lung field.

In contrast, FIG. 6B illustrates an example of a case in which the periphery of the lung field is seen by the blood flow scintigraphic examination and the result of the blood flow scintigraphic examination can prove that a region LAr with a small blood flow volume is present in the upper part of the left lung field.

FIG. 6C is a diagram illustrating an example of a blood flow analysis image in a case in which a frame image corresponding to ventricular end-diastole is used as the reference frame image as in the first method. FIG. 6D is a diagram illustrating an example of a blood flow analysis image in a case in which a frame image corresponding to the ventricular systole of the heart after a heartbeat is generated is used as the reference frame image as in the second method.

As illustrated in FIG. 6C, in a case in which the frame image corresponding to ventricular end-diastole is used as the reference frame image, it is difficult to distinguish the region LAr with a small blood flow volume from a part with a high blood flow volume. In contrast, as illustrated in FIG. 6D, in a case in which the frame image corresponding to ventricular systole is used as the reference frame image, the region LAr with a small blood flow volume is not buried in noise and can be identified. Similar to the image in the blood flow scintigraphic examination illustrated in FIG. 6B, it can be confirmed that the region LAr with a small blood flow volume is present in the upper part of the left lung field.

Figure 7:
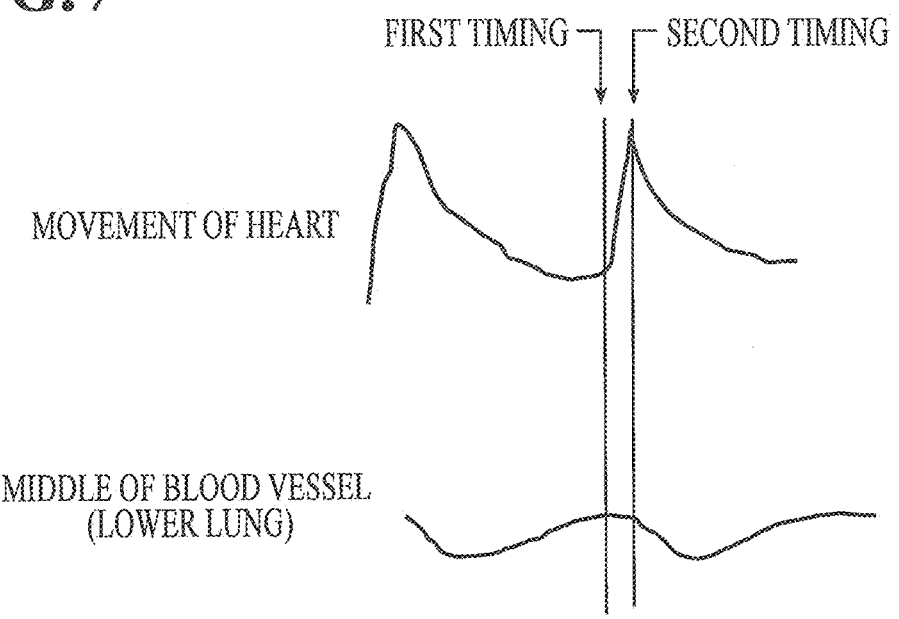
FIG. 7 is a diagram illustrating the relationship between the heartbeat and the movement of a lung blood vessel at the first timing and the second timing.

In the part in which the movement of the organ is large due to the heartbeat, such as the lower lung, particularly, the lower left lung, the lung field is expanded and contracted or translated by the heartbeat, which results in a change in the pixel value. Therefore, in a case in which the frame image corresponding to ventricular end-diastole (see the first timing in, for example, FIG. 7) is used as the reference frame image as in the first method, there is a concern that a value different from a change in blood flow volume will be calculated.

Therefore, as in the second method, the frame image immediately after the heartbeat (see the second timing in, for example, FIG. 7) is set as the reference frame image to minimize the influence of the change in the pixel value.

In this case, for example, it is desirable to set a frame image captured at the time when the heartbeat stops as the reference frame image.

The blood flow arrival start time to the lower left lung starts immediately after a heartbeat. Therefore, a frame image captured at the time when the movement of the heart caused by the heartbeat is equal to or less than a threshold value or a frame image captured a predetermined period of time (for example, 0.2 seconds) after the time when a large cardiac motion occurs may be used as the reference frame image.

As the method for setting the reference frame image in the analysis target setter 52, for example, the following third method is considered.

That is, the reference frame image is set on the basis of a change in the density of region of the lung field in the vicinity of the heart or a change in the position of a blood vessel such as the aorta.

The heartbeat phase can also be detected by measuring the position or size of the heart. However, for example, in the case of a patient with cardiac hypertrophy, it is difficult to measure the position of the heart wall and to correctly recognize a change in the position of the heart. In addition, the difference between the positions of the atria and the ventricles is unclear and the movement of the atria is likely to be misinterpreted as the movement of the ventricles. As a result, the heartbeat phase may not be correctly recognized. Further, it is possible to detect the heartbeat phase to some extent on the basis of a change in the density of the lung field. However, there is a delay from the time of ventricular systole to the blood flow arrival time into the lung field and the degree of delay varies depending on a person and the position of the lung field. In addition, in a case in which there is a disease in the lung field, the heartbeat phase is also affected by the disease. As a result, accuracy is reduced.

Figure 8:
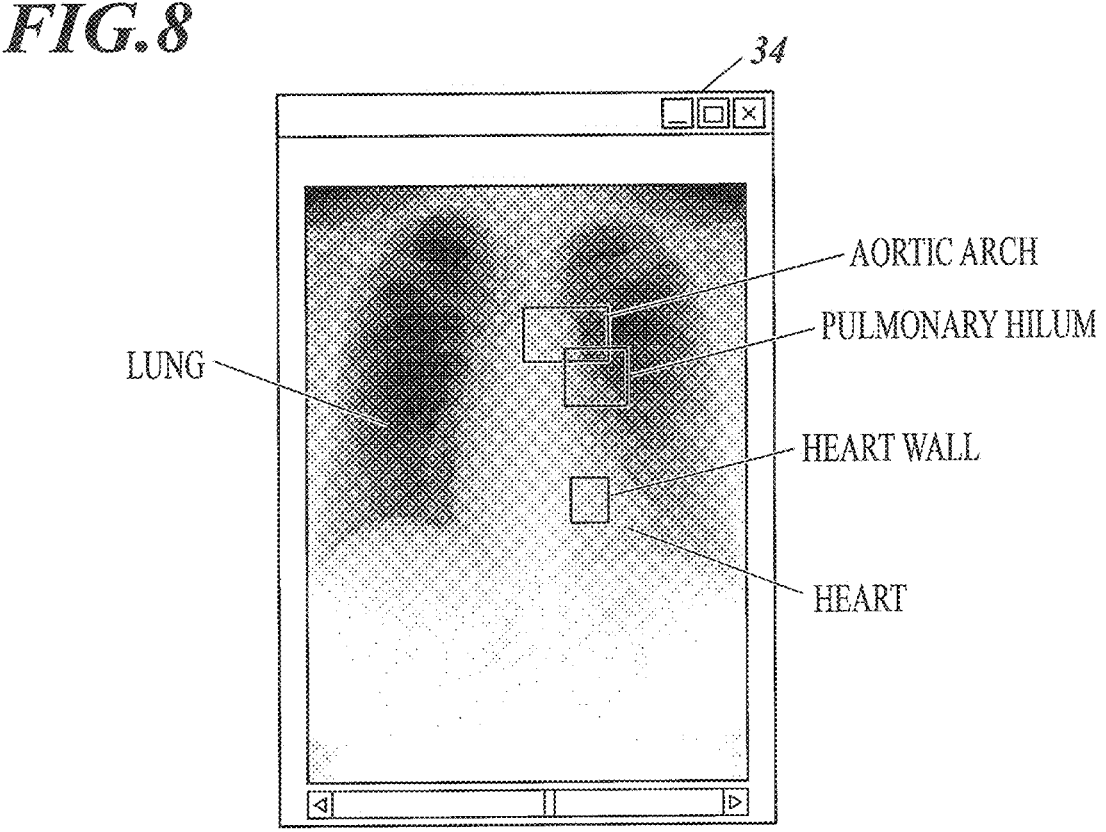
FIG. 8 is a diagram illustrating an example of an X-ray image of the human chest.

Therefore, the third method refers to a change in the density of a region of the lung field in the vicinity of the heart or a change in the position of the blood vessel. As a result, it is possible to correctly recognize the heartbeat phase of the ventricle. More specifically, detecting the movement of, for example, the aortic arch or the pulmonary hilum (see FIG. 8) to detect the heartbeat phase is considered as referring to a change in the position of the blood vessel. More specifically, referring to a change in the density of the region in the vicinity of the heart is to specify the position of the heart, the aortic arch, or the pulmonary hilum (see FIG. 8) and to detect a temporal change in pixel value in a region of the specified part or a region in the vicinity of the specified part to specify the heartbeat phase. It is desirable that, particularly, a lower region of the heart including the ventricle is used as the region in the vicinity of the heart.

It is considered that the position of the heart, the heart wall, the aortic arch, or the pulmonary hilum is calculated by, for example, template matching. In addition, a method for calculating the position of the heart, the heart wall, the aortic arch, or the pulmonary hilum is not limited thereto. Various methods can be used.

In a case in which a change in the density of each structure is used, it is preferable to use a portion in which a frequency component of the cardiac cycle is strong. Therefore, frequency analysis may be performed for each pixel of the dynamic image to select a region range in which the peak of the frequency component is the highest in the assumed heartbeat frequency range. In this case, it is possible to obtain the more stable results by using the frequency analysis in parallel to the template matching, which is preferable.

The heart, the aorta, or the pulmonary hilum may be recognized by the magnitude of the absolute value of the derivative value of the density change. Since the absolute value of the differential value of the density change in ventricular systole is larger than that in ventricular diastole, it is possible to distinguish the ventricle, the aorta, and the pulmonary hilum according to whether a value at which the absolute value of the differential value is the maximum is positive or negative.

Figure 9A:
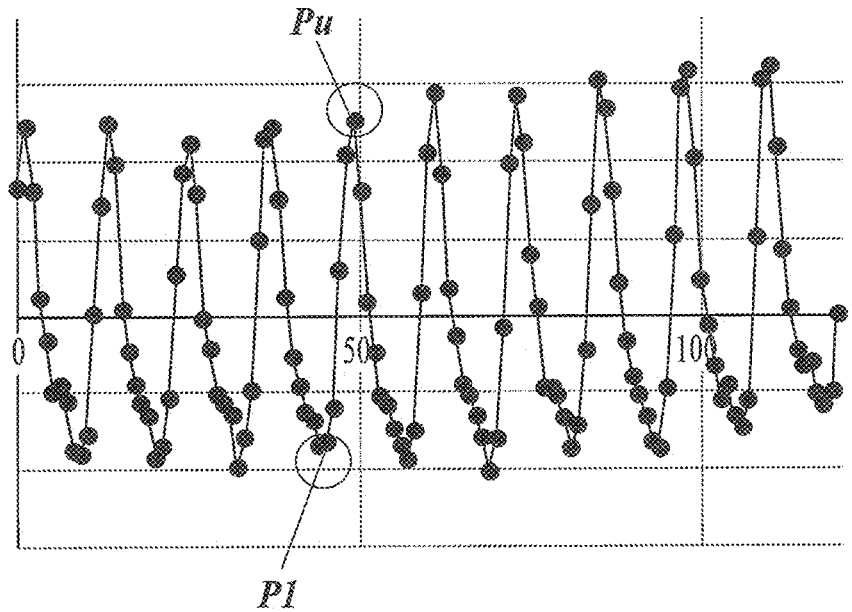
FIG. 9A is a diagram illustrating an example of the waveform of the original image.
Figure 9B:
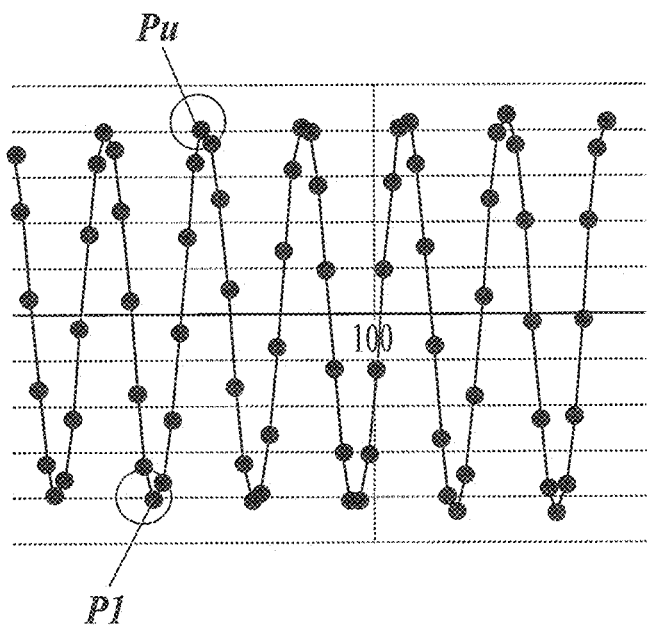
FIG. 9B is a diagram illustrating an example of the waveform of an image after a filtering process.

For example, waveforms illustrated in FIG. 9A or FIG. 9B are obtained by recognizing a change in the position of the heart wall, the aortic arch, or the pulmonary hilum in a predetermined direction (for example, the X direction) or a density change in the heart, a lower region of the heart, the aorta, or the pulmonary hilum.

A local maximum value Pu or a local minimum value P1 is acquired from the waveforms to specify the heartbeat phase. A density change in the heart or the lower region of the heart indicates the waveform of the blood volume of the ventricle, the local minimum value P1 corresponds to the ventricular end-diastole, and the local maximum value Pu corresponds to the ventricular end-systole.

According to the third method, it is possible to accurately calculate the heartbeat phase of the ventricle.

In the density change in the aorta or the pulmonary hilum, the local minimum value P1 corresponds to the ventricular end-systole and the local maximum value Pu corresponds to the ventricular end-diastole.

In a case in which a change in the position of the heart wall is seen and a coordinate system is configured such that the coordinate value of the position becomes smaller as the position becomes further away from the center of the heart, the local minimum value P1 corresponds to the ventricular end-diastole and the local maximum value Pu corresponds to the ventricular end-systole. In a case in which a change in the position of, for example, the aortic arch or the pulmonary hilum is seen and the coordinate system is configured such that the coordinate value of the position becomes larger as the position becomes further away from the center of an aortic arch region or a pulmonary hilum vessel region, the local minimum value P1 corresponds to the ventricular end-diastole and the local maximum value Pu corresponds to the ventricular end-systole.

The waveform of the density change may be the pixel value of X-ray transmission or the waveform subjected to logarithmic conversion in the logarithmic conversion processor 53. In addition, in a case in which an image is divided into small blocks, the waveform of the density change may be a waveform after the blocking process. In a case in which a filtering process is performed, a waveform after the filtering process may be used.

It is desirable to use the waveform after the blocking process or the filtering process in order to maintain consistency with the blood flow analysis image and to stably obtain the local maximum value Pu and the local minimum value P1 from the waveform without noise.

For the consistency with the blood flow analysis image, for example, in a case in which the heartbeat phase to be specified is the reference frame image, the ventricular end-systole is the local minimum value P1 of the density waveform of the ventricle.

FIG. 9A is a diagram illustrating an example of the waveform of the original image and FIG. 9B is a diagram illustrating an example of the waveform after the filtering process.

As illustrated in FIG. 9A and FIG. 9B, in some cases, the local minimum value P1 in the waveform of the original image is a frame that is not the local minimum value P1 after the filtering process. Therefore, the local minimum value P1 may be selected from the waveform after the filtering process.

Figure 10A:
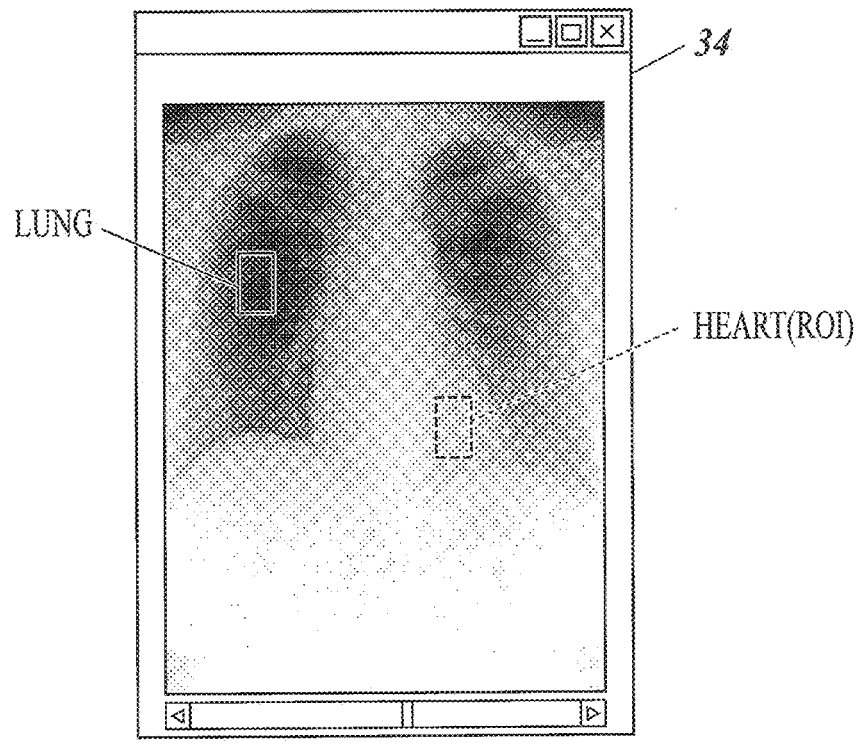
FIG. 10A is a diagram illustrating an example in which a region of interest is set in a ventricular region of the heart.

For example, as illustrated in FIG. 10A, a region of interest ROI may be set in a ventricular region of the heart and a frame image in which the density value of the region of interest ROI is the minimum may be selected as the reference frame image.

The minimum density value means that the amount of blood in the ventricular region as the region of interest ROI is the maximum.

Figure 10B:
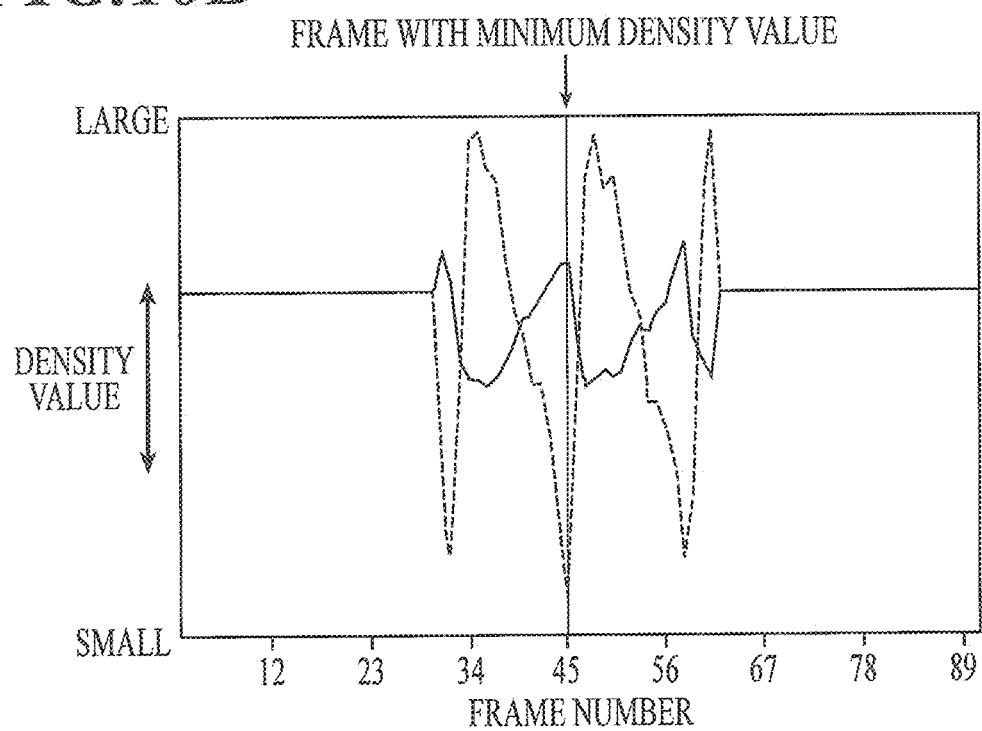
FIG. 10B is a graph illustrating a temporal change in a value obtained by applying a high-pass filter to a density value.

For example, in the example illustrated in FIG. 10B, a frame image of frame number 45 has the minimum density value and is selected as the reference frame image.

In a case in which there are a plurality of heartbeats, a heartbeat frequency may be extracted in advance by frequency analysis and a combination of the maximum value and the minimum value in units of the cardiac cycle. For example, in a case in which the frame rate of a moving image is 15 fps and the cardiac cycle is 1.2 Hz, a pair of ventricular end-diastole (minimum value) and ventricular end-systole (maximum value) exists in a frame cycle of 12.5.

In this case, in each frame, ventricular end-diastolic likeness is quantified. Among the combinations of the frame images with a frame cycle of 12.5, a frame image with the "highest ventricular end-diastole likeness" may be used as a frame corresponding to ventricular end-diastole. A frame corresponding to ventricular end-diastole in a certain cycle may be selected as the reference frame image.

The term "ventricular end-diastole likeness" may be expressed using a frame with the local minimum value or a frame with a large differential value between the subsequent several frames.

For other heartbeat phases, for example, in a case in which there is a frame corresponding to the relative position between the ventricular end-diastole and the ventricular end-systole, that is, an intermediate frame, the heartbeat phase is mid-systole and a frame image including the initial movement of contraction can be selected as the reference frame image.

An absolute temporal change based on the ventricular end-systole or the ventricular end-diastole, for example, 0.2 seconds may be extracted as ventricular mid-systole (0.2 seconds after the ventricular end-systole) or ventricular early-diastole (0.2 seconds after the ventricular end-systole).

For example, the heartbeat phase varies depending on the person. For example, the heartbeat phase is usually disturbed in the case of a heart failure. Therefore, it is preferable to decide an appropriate heartbeat phase selection method according to the purpose.

The frame image to be set as the reference frame image depends on the state of the blood flow desired to be detected. For example, in cases other than a case in which the blood flow state of a peripheral blood vessel is seen, a frame image captured at timings other than the above-mentioned timing may be used as the reference frame image.

It is preferable to set a frame image in which the amount of movement caused by, for example, a body motion or breathing is small as the reference frame image.

In a case in which the imaging console 2 calculates and sets the amount of movement for each frame image or the range (analysis target frame range) of frame images suitable for analysis, the image acquirer 51 may also acquire the information from the imaging console 2. In this case, the analysis target setter 52 may set the analysis target frame range on the basis of the information and may set a frame image as the reference frame image from the analysis target frame range.

The logarithmic conversion processor 53 performs logarithmic conversion for the pixel value of the dynamic image acquired by the image acquirer 51 to create a logarithmically converted image.

The pixel value (that is, a pixel signal value) of the dynamic image of a living body having a heartbeat which has been acquired by the image acquirer 51 is a density value. A large pixel value means high X-ray transmittance and a small pixel value means low X-ray transmittance.

That is, in a portion in which a large amount of blood flows, the X-rays are blocked by the blood flow and the pixel value is small. Conversely, in a portion in which a small amount of blood flows, the X-ray transmittance is high and the pixel value is large (for example, see FIG. 2).

The X-rays incident on the living body are blocked not only by blood but also by various structures (for example, bones, such as the ribs, or various organs other than the lungs) present in the X-ray transmission direction. Therefore, radiation transmittance and the pixel value also change.

The relationship between an X-ray dose (input) I0 and the amount of X-rays transmitted (output) I is expressed by the following Expression 1 and, assuming that parameters of a target material to be transmitted are $\mu$, $\rho$, and X, the relationship between the input and output of X-rays is determined by a combination of $\mu$, $\rho$, and X:

$$I = I0 \times \exp[-\mu \cdot \rho \cdot X] \qquad \text{Expression 1}$$

$\mu$: mass absorption coefficient [cm$^{2/g}$]
$\rho$: density [g/cm$^3$]
X: object transmission distance [cm]

Figures 11A, 11B:
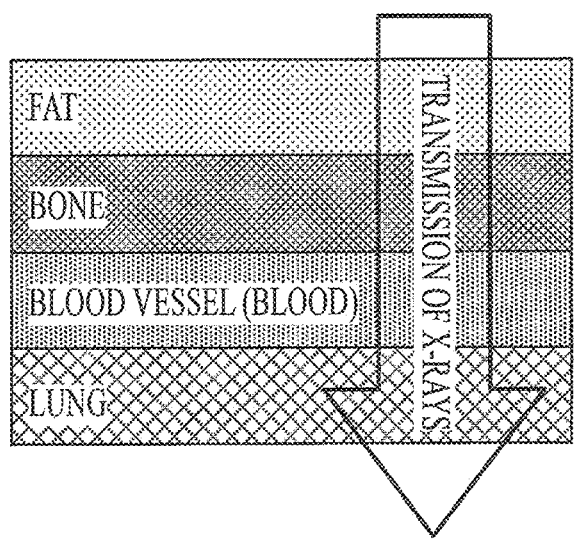
FIG. 11A is a table illustrating a mass absorption coefficient and density of the main structures in a living body.
FIG. 11B is a diagram schematically illustrating the main structures through which X-rays are transmitted to the lung field.

Here, FIG. 11A illustrates "$\mu$" (mass absorption coefficient) and "$\rho$" (density) of the main structures in a living body. As illustrated in FIG. 11B, since X-rays are transmitted to the lung field through structures, such as fat, bones, and blood vessels (blood), it is necessary to consider the influence of the structures in the living body in order to correctly recognize a change in the amount of blood in the lung field. Therefore, various measures are required. For example, it is necessary to perform imaging for a predetermined period of time in a state in which the object is stationary as much as possible.

For example, a state model is assumed in which the thicknesses of fat, bones, and the lung are constant and only the thickness of blood vessels (blood) changes in two frames. In the state model, for example, in a case in which an X-ray output value in each frame is I, an X-ray output value in the reference frame is I', the thicknesses (that is, the transmission distance of X-rays through the object) of fat, bones, blood vessels (blood), and the lung are Xa, Xb, Xc, and Xd, respectively, and the thicknesses of fat, bones, and the lung at each time are constant, the difference between the logarithms of the X-ray output values at two times can be represented by the following Expression 2, regardless of an incident dose I0 which is constant regardless of time:

$$\log I - \log I' =$$
$$\log(I\_0 * \exp[-\mu a \cdot \rho a \cdot Xa] * \exp[-\mu b \cdot \rho b \cdot Xb] * \exp[-\mu c \cdot \rho c \cdot Xc] *$$
$$\exp[-\mu d \cdot \rho d \cdot Xd]) - \log(I\_0 * \exp[-\mu a \cdot \rho a \cdot Xa] *$$
$$\exp[-\mu b \cdot \rho b \cdot Xb] * \exp[-\mu c \cdot \rho c \cdot Xc'] * \exp[-\mu d \cdot \rho d \cdot Xd]) =$$
$$\{\log(I\_0) + (-\mu a \cdot \rho a \cdot Xa) + (-\mu b \cdot \rho b \cdot Xb) + (-\mu c \cdot \rho c \cdot Xc) +$$
$$(-\mu d \cdot \rho d \cdot Xd)\} - \{\log(I\_0) + (-\mu a \cdot \rho a \cdot Xa) + (-\mu b \cdot \rho b \cdot Xb) +$$
$$(-\mu c \cdot \rho c \cdot Xc') + (-\mu d \cdot \rho d \cdot Xd)\} = -\mu c \cdot \rho c \cdot (Xc - Xc')$$

Expression 2

A formula for logarithmic conversion can be expressed as Expression 3 and is substituted into Expression 2 to obtain Expression 4:

$$\log M - \log N = \log(M/N) \qquad \text{Expression 3}$$

$$\log I - \log I' = \log(I/I') \qquad \text{Expression 4}$$

As such, logarithmic conversion is performed for the pixel value of the dynamic image to represent the relationship between the input and the output of the X-rays with a value that is proportional to a change in the amount of blood per unit area in the X-ray transmission direction. Therefore, it is possible to physically calculate a component that is proportional to a pulsatility change of the blood flow volume. This configuration makes it possible to present the state of a blood flow to the doctor in an intuitive manner and to provide clinically meaningful images and numerical values to, for example, the doctor.

Here, $\mu c$ and $\rho c$ may be calculated to indicate an absolute change in the thickness of the blood vessel (change in the amount of blood).

As a calculation method, the logarithmic conversion process may not be performed first, but may be performed after the ratio of pixel values is calculated as illustrated in Expression 4. In this case, the denominator I' corresponds to the amount of X-rays transmitted (output) in the reference frame. In this embodiment, a case in which the process of obtaining the difference is performed after the logarithmic conversion process is described as an example. In this case, the logarithmic conversion process may be performed after the ratio of the pixel values is calculated. In addition, the logarithmic conversion processing may not be performed after the ratio of pixel values is calculated. In this case, the value is not proportional to a physical quantity, but the magnitude relationship is established. In addition, in a case in which the ratio is calculated, the logarithmic conversion can be omitted and the values of $\mu$ and $\rho$ are not required. In addition, the numerical values that are easy for the doctor to understand intuitively are obtained. Therefore, this method is also desirable. For example, the percentage of the lung blood flow is about 1% to 2%.

As a calculation method for logarithmic conversion, logI is simply described here. However, for example, the following expression (Expression 5) may be used:

$$L = a + b*\log(c*I + d) \qquad \text{Expression 5}$$

Here, L is a pixel value after logarithmic conversion and variables a, b, c and d are parameters.

In addition, contrary to the amount of blood flowing into the entire lung field, the same calculation can be performed by adding up the output of the entire heart region. Furthermore, in a case in which the number of heartbeats is also calculated from the dynamic image, the output of the heart is integrated with the number of heartbeats to obtain a value that means the output of the heart for one minute, which can be useful for diagnosis.

The lung field is divided into right and left regions. For example, the lung field is divided into three regions, that is, upper, middle and lower regions and each region is presented as numbers. In this case, it is also possible to analyze the difference between the regions in the organ.

In the method that represents each region with numerical values, it is not necessary to analyze the entire image and calculations may be performed only for a necessary region. In this case, it is possible to reduce unnecessary calculation time.

As a region extraction method, various known methods including template matching can be used.

The blood flow analyzer 54 calculates the difference or ratio between the reference frame image and another frame image to generate a blood flow analysis image.

As described above, the analysis target setter 52 according to this embodiment sets the reference frame image to at least one of the X-ray dynamic image (the original X-ray image) and the logarithmically converted image. The blood flow analyzer 54 calculates the difference between the reference frame image set by the analysis target setter 52 and a comparative frame image which is another frame image or the ratio of the pixel value of the reference frame image to the pixel value of the comparative frame image and generates a blood flow analysis image on the basis of the difference or the ratio.

That is, in a case in which the analysis target setter 52 sets one frame image among the X-ray dynamic images as the reference frame image, the blood flow analyzer 54 calculates the difference between the X-ray dynamic images or the ratio of the pixel values of the X-ray dynamic images, using the comparative frame image as one frame image among the X-ray dynamic images. In addition, in a case in which the analysis target setter 52 sets one frame image among the logarithmically converted images as the reference frame image, the blood flow analyzer 54 calculates the difference between the logarithmically converted images or the ratio of the pixel values of the logarithmically converted images, using the comparative frame image as one frame image among the logarithmically converted images.

The blood flow analyzer 54 according to this embodiment calculates the difference between the reference frame image and the comparative frame image such that the pixel value of each frame image is a representative value of the block size that is equal to or greater than 7 mm.

As described above, in this embodiment, in order to perform blood flow analysis while excluding artifacts as much as possible, imaging is performed in a breath-hold state, or blood flow analysis is performed by setting a range in which frame images with a small amount of movement among a plurality of captured frame images are continuous as the analysis target frame range.

However, even in a case in which imaging is performed in a breath-hold state, the blood vessels are moved in the X direction and the Y direction by the beating of the heart and a change in pixel value does not indicate a change in blood flow volume, but may indicate the movement of the blood vessels. In particular, while the change in pixel value due to the change in blood volume is small, the change in pixel value due to the movement of the blood vessels is large. Therefore, in a case in which the change in pixel value due to the movement of the blood vessels is picked up, it is difficult to correctly recognize the change in blood volume.

Therefore, the diameter and the amount of movement of the blood vessels were measured. The measurement results proved that, in the case of many healthy persons and patients, particularly, in the wide lung field region of the pulmonary hilum or the left lung, a blood vessel with a diameter of about 2 mm was moved about 5 mm in the X and Y directions by the beating of the heart.

In a case in which a thin blood vessel having a diameter of about 2 mm moves in and out of the analysis range in this manner, the percentage of a change in pixel value is about 5%. In contrast, for example, a change in blood volume in the lung field corresponds to 1% to 2% in terms of the percentage of the change in pixel value. Therefore, there is a concern that a change in blood volume which is completely different from the change in blood volume to be recognized will be calculated in a case in which it is affected by the movement of blood vessels.

For this reason, in a case in which the difference or ratio between the reference frame image and the comparative frame image is calculated and the reference frame image and the comparative frame image are divided into small blocks, it is preferable that the blood flow analyzer 54 sets the block size to be equal to or greater than 7 mm (=a blood vessel diameter of 2 mm +a movement width of 5 mm).

FIG. 12A to FIG. 12D are diagrams schematically illustrating blood vessels and the relationship between the movement width of the blood vessels and small blocks.

Figure 12A:
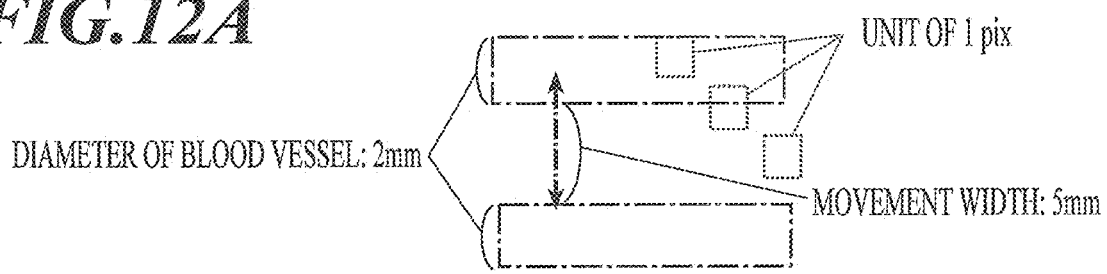
FIG. 12A is a diagram illustrating a blood vessel and the relationship between the movement width of the blood vessel and a block size and illustrates a case in which the block size is one pixel.
Figure 12B:
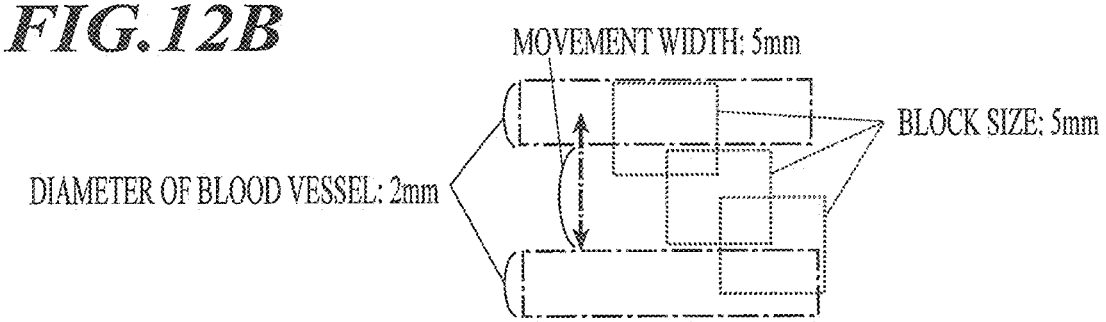
FIG. 12B is a diagram illustrating a blood vessel and the relationship between the movement width of the blood vessel and a block size and illustrates a case in which the block size is 5 mm.

For example, as illustrated in FIG. 12A or FIG. 12B, in a case in which the size of the small block is equal to or less than 7 mm (FIG. 12A illustrates a case in which the size of the small block is 1 pix and FIG. 12B illustrates a case in which the size of the small block is 5 mm), an analysis portion falls within the range affected by the movement of the blood vessel.

Figure 12C:
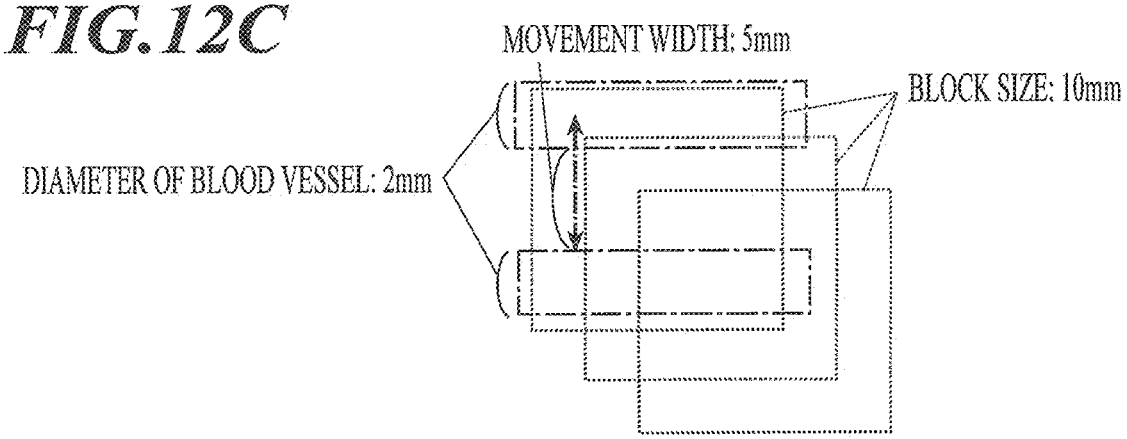
FIG. 12C is a diagram illustrating a blood vessel and the relationship between the movement width of the blood vessel and a block size and illustrates a case in which the block size is 10 mm.

In contrast, FIG. 12C illustrates an example in which the size of the small block is equal to or greater than 7 mm (10 mm in the example illustrated in FIG. 12C). In a case in which the sum of the diameter of the blood vessel and the amount of movement of the blood vessel is equal to or less than the size of the small block, the pixel values (or the logarithmic values) of the reference frame image and the comparison frame image are substituted with representative values in the small block, that is, means, medians, or statistical values to reduce the influence of the movement of the blood vessels.

Figure 12D:
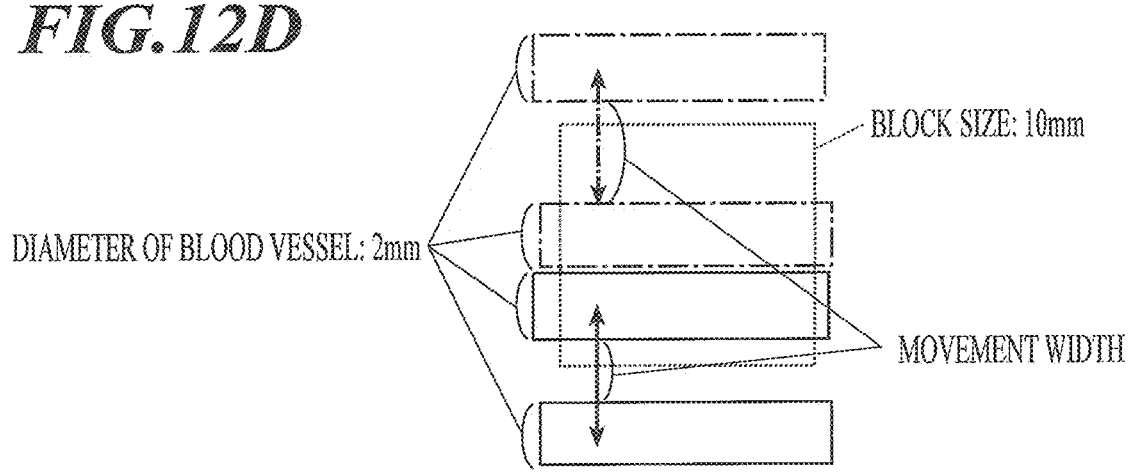
FIG. 12D is a diagram illustrating a blood vessel and the relationship between the movement width of the blood vessel and a block size and illustrates a case in which the block size is 10 mm.

FIG. 12D illustrates a case in which the size of the small block is 10 mm and a plurality of blood vessels (two blood vessels in FIG. 12D) are moved largely to come in and out of the small block. However, in a case in which other blood vessels are present around the blood vessel as in the example illustrated in FIG. 12D, the influence of the movement of the blood vessel in and out of the small block on the result of blood flow analysis is reduced.

As such, in a case in which the difference or ratio between the reference frame image and the comparative frame image is calculated and the size of the small block is greater than the sum of the diameter of the blood vessel and the amount of movement of the blood vessel (for example, the size of the small block is equal to or greater than 7 mm and is 10 mm in the example illustrated in FIG. 12C), the representative values, such as means, medians, or statistical values, of the pixel values of the small blocks are used as the pixel values (or the logarithmic values) of the reference frame image and the comparison frame image to reduce artifacts caused by the movement of the blood vessel and to accurately recognize a change in blood volume.

In a case in which the size of the small block is too large, the image is rough and it is difficult to perform detailed blood flow analysis. For this reason, it is preferable that the size of the small block is set to such an extent (for example, 7 mm or more and 20 mm or less) that artifacts can be reduced and the required image quality can be ensured.

In this embodiment, as described above, imaging is performed in a breath-hold state, or blood flow analysis is performed by setting a range in which frame images with a small amount of movement among a plurality of captured frame images are continuous as the analysis target frame range.

However, for example, even in a case in which imaging is performed in a breath-hold state, the pixel value may be changed by the unconscious movement of the body. As a result, it is difficult to correctly recognize a change in blood flow volume.

For this reason, in a case in which the blood flow analyzer 54 calculates the difference or ratio between the reference frame image and the comparative frame image, it is preferable to perform a filtering process of limiting a frequency component in the time direction for each pixel value.

For example, noise can be suppressed by obtaining numerical values limited to only a density change or movement caused by the beating of the heart (heartbeat) using frequency processing.

Figure 13A:
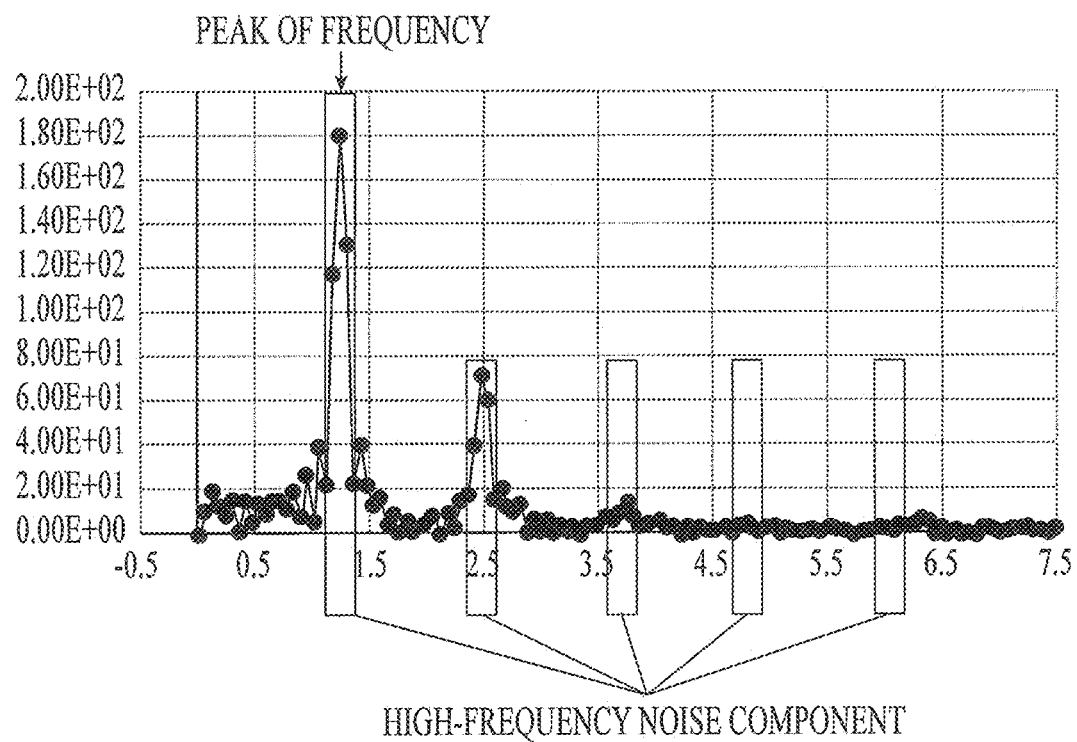
FIG. 13A is a graph illustrating an example of the frequency characteristics of the heart.
Figure 13B:
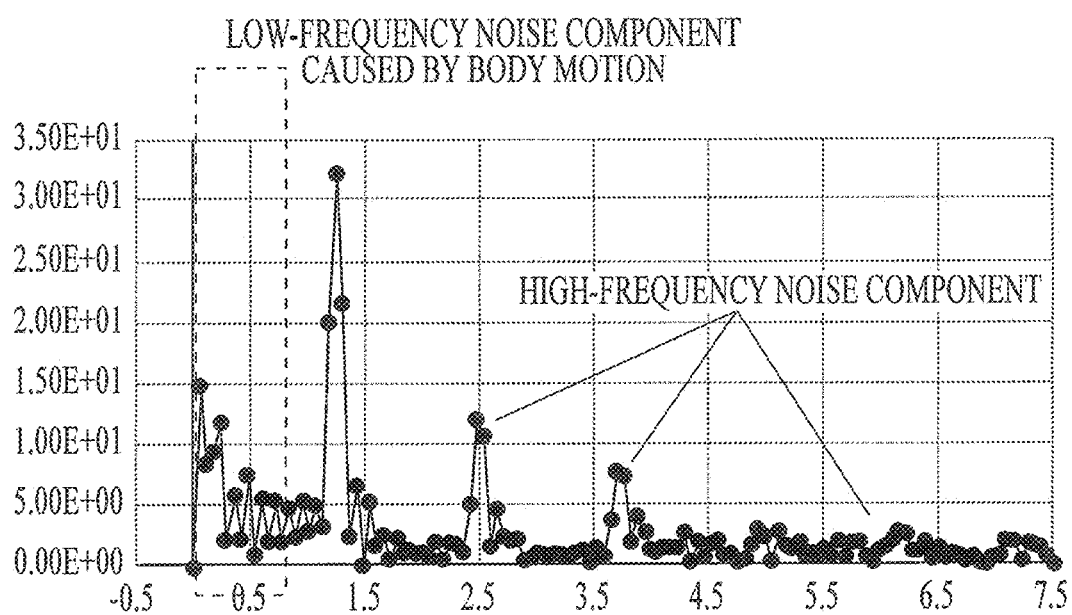
FIG. 13B is a graph illustrating an example of the frequency characteristics of the lung field.

FIG. 13A is a graph illustrating the frequency characteristics of the heart (left ventricle) and FIG. 13B is a graph illustrating the frequency characteristics of a certain portion in the lung field.

Low-frequency components generated by, for example, a body motion are included as noise in the image. For this reason, it is preferable to perform a high-pass filtering process that cuts frequency components lower than the heartbeat frequency. In this case, it is possible to prevent the low-frequency components generated by, for example, a body motion from becoming noise.

A bandpass filtering process limited only to the heartbeat frequency may be performed. In this case, it is also possible to cut high-frequency noise caused by, for example, panel noise.

As a method, first, a heart (left ventricle) region is extracted from an image and frequency analysis, such as Fourier transform, is performed for data of a temporal change in the density of the heart region to calculate the peak (maximum value) of the frequency (see FIG. 13A).

In a case in which the amount of low-frequency movement (that is, for example, a body motion) is large, the peak of the frequency becomes a low frequency. Therefore, it is preferable that the frequency analysis is performed for the frame range (analysis target frame range) captured in a breath-hold state in advance.

The analysis target may be limited to a constant frequency range. For example, a frequency less than 0.8 Hz is excluded.

The heart (left ventricle) region may be extracted by a method such as template matching. In this case, a portion on the heart wall may be extracted to extract frequency components generated by the movement of the heart wall.

For example, in the case of a bandpass filter, the peak of the frequency is calculated to decide a peak frequency range in which a heartbeat signal is present. For the peak frequency range, for example, the range of a peak frequency of ±0.1 Hz may be decided as a fixed value. Alternatively, the width of the peak frequency range may be dynamically changed depending on the distribution of frequency components.

In this case, only the fundamental frequency of the heartbeat can be extracted, but it is possible to obtain a stable blood flow analysis image without high-frequency noise.

The frequency range of harmonics may also be extracted as the range in which a signal is present. In this case, for example, the range of a peak frequency×N±0.1 Hz may be decided as a fixed value or the width of the frequency range may be dynamically changed depending on the distribution of frequency components.

Figure 14A:
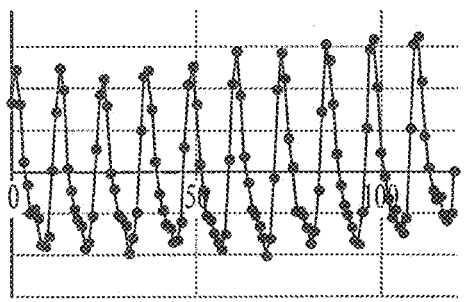
FIG. 14A is a diagram illustrating an example of the waveform of the input original image.
Figure 14B:
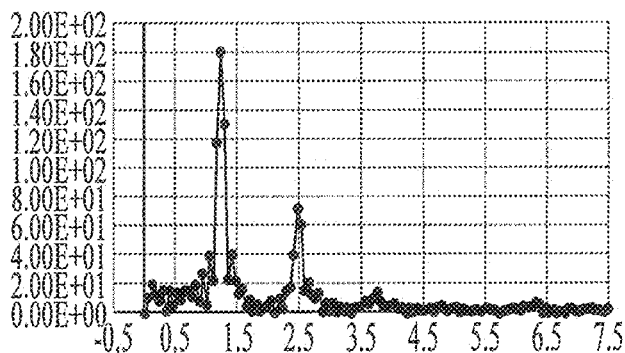
FIG. 14B is a diagram illustrating an example of a waveform after Fourier transform.
Figure 14C:
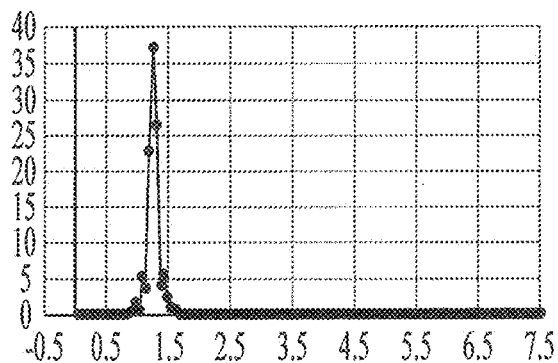
FIG. 14C is a diagram illustrating an example of a waveform after the filtering process.

The filtering process may be performed by the following method. For example, in a case in which there is input data (waveform) illustrated in FIG. 14A, Fourier transform is performed for the input data to convert the input data into a frequency space illustrated in FIG. 14B. Then, a desired frequency filtering process is performed in the frequency space to extract a signal in the desired frequency range as illustrated in FIG. 14C. In addition, inverse Fourier transform is performed for the signal (see FIG. 14D).

In addition to Fourier transform, for example, DCT may be used.

Further, for example, the filtering process may be performed by creating an array of convolution coefficients designed to cut a desired frequency in advance and performing a convolution operation.

The first several frames and the last several frames (for example, the first 15 frames and the last 15 frames in the case of a convolution operation with an array of 16 coefficients) of the analysis target frame range form frame ranges with low reliability (see hatched portions in FIG. 14D) due to the influence of the transient response of the filtering process. It is preferable to remove the frame range with low reliability from the blood flow analysis target. The blood flow analysis image after the filtering process is basically a moving image repeated in a cardiac cycle. Therefore, it is desirable that the output is equal to or greater than two cardiac cycles such that a stable output can be confirmed.

Figure 14D:
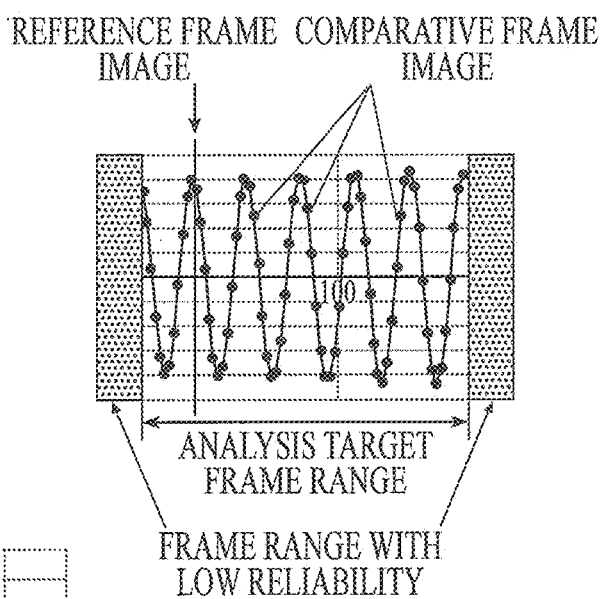
FIG. 14D is a diagram illustrating an example of a waveform after inverse Fourier transform.

For example, in a case in which the reference frame image is set as illustrated in FIG. 14D, each frame image in the analysis target frame range is set as the comparative frame image and the difference or ratio between the reference frame image and the comparative frame image is calculated to obtain a blood flow analysis image for each comparative frame image.

As such, the filtering process is performed before blood flow analysis is performed. Therefore, even in a case in which the dynamic image includes, for example, movement caused by a body motion which becomes low-frequency noise or panel noise which becomes high-frequency noise, it is possible to suppress the influence of the noise on blood flow analysis and to obtain a blood flow analysis image that can be more accurately viewed.

The display controller 55 controls the displaying of the display 34.

In this embodiment, in a case in which the blood flow analyzer 54 calculates the difference between the reference frame image and the comparative frame image to obtain a difference image as the blood flow analysis image, the display 34 displays the difference image as a functional image.

In this case, the display controller 55 controls the displaying of the display 34 such that colors vary according to whether a difference value (the pixel value of the difference image) is positive or negative. In addition, the display controller 55 performs control such that the absolute value of the difference value is reflected in the displaying of the display 34 so as to be associated with parameters other than the color.

In this embodiment, the difference value in a case in which the blood flow analyzer 54 calculates the difference between the reference frame image and the comparative frame image to obtain a difference image as the blood flow analysis image has been described. However, the same process as described above is performed for the ratio (ratio value) in a case in which the blood flow analyzer 54 calculates the difference between the reference frame image and the comparative frame image to obtain a ratio value image as the blood flow analysis image. Therefore, the description thereof will not be repeated.

That is, a ratio is calculated, using the pixel value I' of the reference frame image as the denominator and the pixel value I of the comparative frame image as the numerator, and the difference between the ratio and 1.0 is represented by a ratio value Rat (Rat=I/I'−1.0 or Rat=log(I/I')−1.0). The ratio value can be treated almost the same as the difference value. Therefore, in the case of the ratio, the display controller 55 may control the displaying of the display 34 such that colors vary according to whether the ratio value is positive or negative. In addition, the display controller 55 may control the displaying of the display 34 such that the absolute value of the ratio value is reflected in the displaying of the display 34 so as to be associated with parameters other than the color.

That is, even in a case in which the difference image (or the ratio value image) as the blood flow analysis image is displayed on the display 34 without any change, it is difficult for anyone to immediately understand the state indicated by the image.

For this reason, it is desirable to display the difference image (or the ratio value image) as an image that is easier to see.

The blood flow analyzer 54 according to this embodiment displays, as the functional image, an image obtained by performing color coding for the difference image according to the state of a blood flow such that the state of, for example, the blood flow can be easily understood on the display 34.

Figure 15A:
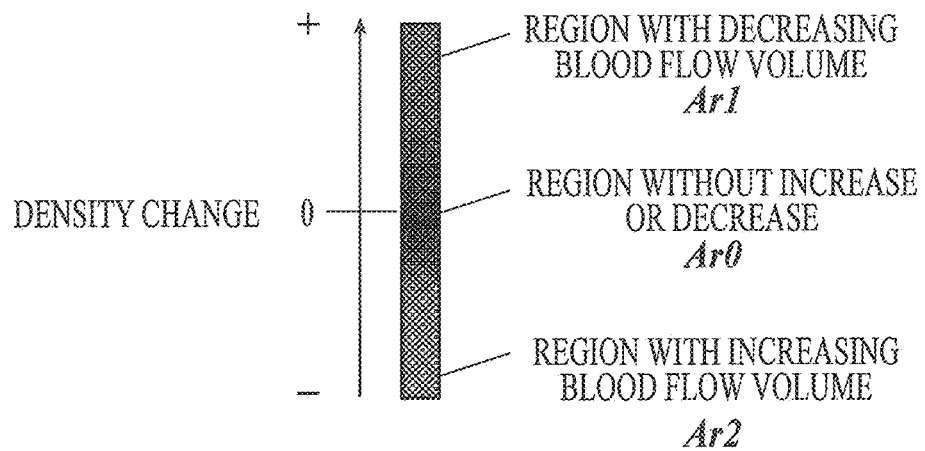
FIG. 15A is a diagram illustrating a change in the density value and correspondence to region division.

Specifically, as illustrated in FIG. 15A, colors vary according to whether the difference value (or the ratio value) is positive or negative and the absolute value of the difference value (or the ratio value) is associated with parameters other than the color.

Figure 15B:
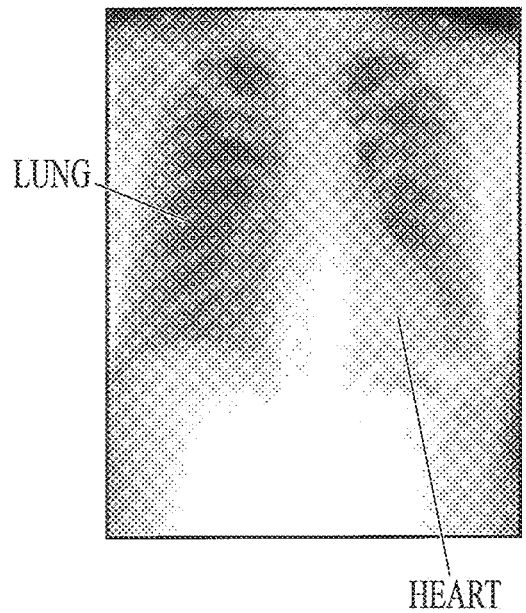
FIG. 15B is a diagram illustrating an example of an X-ray image of the human chest.
Figure 15C:
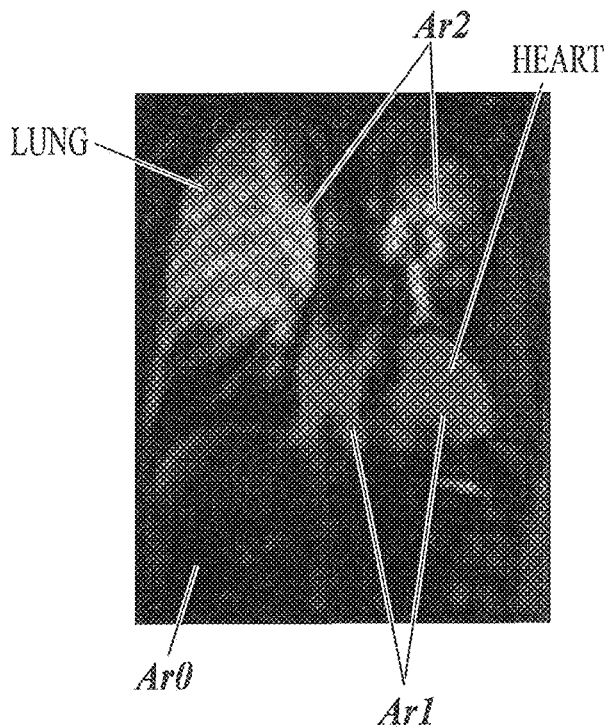
FIG. 15C is a diagram illustrating an example of a blood flow analysis image.

FIG. 15B illustrates an example of the frame image forming the dynamic image and FIG. 15C illustrates an example of the functional image of a difference image corresponding to the frame image illustrated in FIG. 15B.

For example, in the difference image, in a case in which the reference frame image is compared with the comparative frame image, a region in which there is no increase or decrease in blood flow volume (that is, there is no change in density value) is referred to as a region Ar0 with no increase or decrease, a region in which the blood flow volume decreases (that is, the difference value is positive and the density value is large) is referred to as a region Ar1 with a decreasing blood flow volume, and a region in which the blood flow volume increases (that is, the difference value is negative and the density value is small) is referred to as a region Ar2 with an increasing blood flow volume.

Then, the display controller 55 displays the region Ar1 with a decreasing blood flow volume and the region Ar2 with an increasing blood flow volume in different colors on the display 34 such that the region Ar1 with a decreasing blood flow volume in which the difference value is positive is expressed in a cold color, such as blue, and the region Ar2 with an increasing blood flow volume in which the difference value is negative is expressed in a warm color, such as red.

The display of the colors on the display 34 makes it possible to display a functional image that enables the user to recognize the state of the blood flow from the color at a glance.

In a case in which the reference frame image and the comparative frame image are compared and the difference therebetween is zero, the images are preferably expressed in an achromatic color. For example, the images are expressed in black. In this case, the color of the blood flow is more clearly visible, which is desirable.

In this embodiment, the example in which the display controller 55 associates the absolute value of the difference value (or the ratio value) with parameters other than the color (hereinafter, the difference value will be described as an example and the ratio value is treated in the same way as the difference value as described above).

The parameters other than the color include at least one of the intensity, saturation, and brightness of colors and a combination thereof. For example, in a case in which there is an image illustrated in FIG. 16A, the region Ar0 with no increase or decrease, the region Ar1 with a decreasing blood flow volume, and the region Ar2 with an increasing blood flow volume are expressed in different colors of black, blue, and red, respectively. Then, for example, the saturation and brightness of each color are determined according to the absolute value of each difference value.

Figures 16A, 16B:
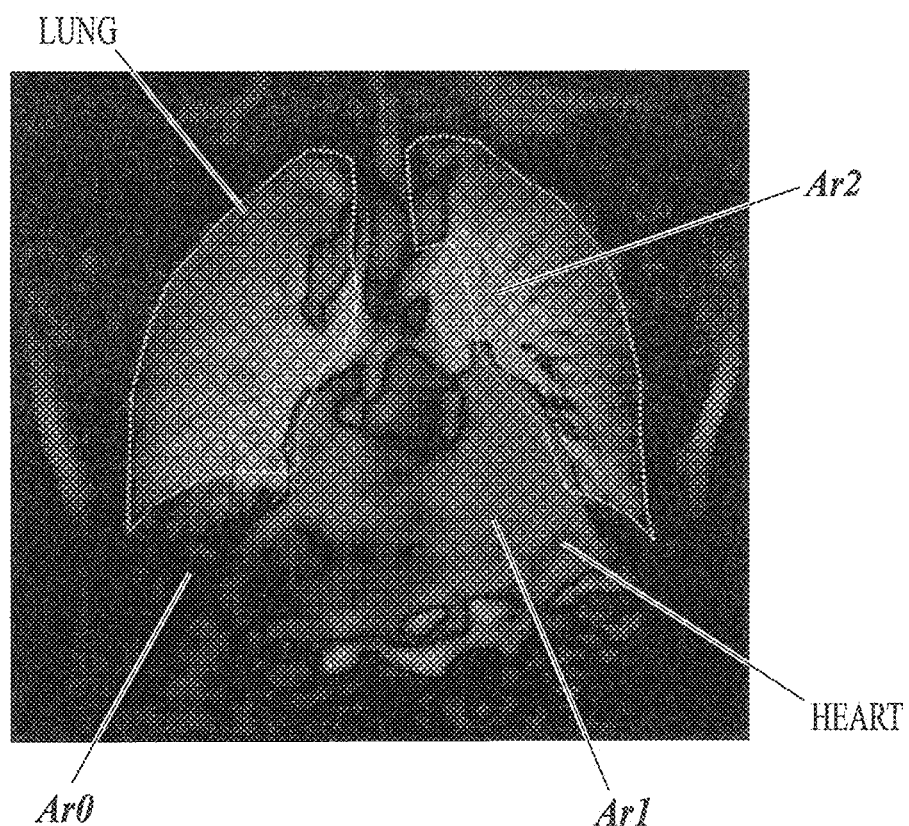
FIG. 16A is a diagram illustrating an example of the blood flow analysis image.
FIG. 16B is a diagram illustrating an example of color coding corresponding to a difference value.

For example, as illustrated in FIG. 16B, R, G, and B values in a case in which the difference value is −1000 are 255, 0, and 0, respectively, R, G, and B values in a case in which the difference value is −500 are 255, 0, and 0, respectively, R, G, and B values in a case in which the difference value is −100 are 50, 0, and 0, respectively, and R, G, and B values in a case in which the difference value is 0 are 0, 0, and 0, respectively. This holds for, for example, R, G, and B values in a case in which the difference value is 1000.

In a case in which the difference value is X and X is negative, $R=|X|*\alpha$ and $G=B=0$ are established. In a case in which X is positive, $B=|X|*\alpha$ and $R=G=0$ are established.

Here, $\alpha$ is an adjustable parameter and is 0.5 in the example illustrated in FIG. 16B.

An upper limit is provided and a value equal to or greater than 255 is corrected to 255.

In a case in which this expression range (upper limit) varies depending on a person, it is difficult to understand the difference between persons in the same way. Therefore, it is desirable to use the same value without any exception. The use of the uniform expression range (upper limit) makes it possible to recognize the absolute difference in the cardiac output at the same time and to improve the efficiency of diagnosis.

It is possible to obtain a spatial blood volume change map with a moving image by converting the difference image into a color on the basis of a numerical value that is proportional to a change in blood volume.

In this embodiment, the change in blood flow volume is displayed on the display 34 so as to be visible. However, the invention is not limited to.

For example, changes in the absolute blood volume in the entire lung field may be added up for each patient or each captured moving image and then presented as numbers. In this case, the value means a cardiac output and can be used for diagnosis.

However, the cardiac output is largely different depending on the person. Therefore, in the case of a person with a very small blood flow signal or a person with a very large blood flow signal, there is a problem that visibility is reduced.

Therefore, in this case, it is desirable that the user operates and sets the upper limit or appropriately corrects a prescribed value in a case in which the prescribed value has already been set.

For example, preferably, a scroll bar (not illustrated) is disposed on the display 34 and is displayed in parallel to an image such that the user can adjust the image while checking the image.

Some upper limits for the persons whose blood flow signals are significantly different from the normal ones may be determined and the mode with different upper limits may be selected by buttons to change the upper limits.

This configuration makes it possible to understand the absolute value of the cardiac output and to maintain the visibility of a blood flow distribution in a case in which the user knows how to view each mode.

A case in which the region Ar1 with a decreasing blood flow volume in which the difference value is positive is expressed in a cold color, such as blue, and the region Ar2 with an increasing blood flow volume in which the difference value is negative is expressed in a warm color, such as red, has been described above. However, there are upper limits in a case in which the regions are expressed only in red and blue. Therefore, different colors among the same warm colors or the same cold colors may be used to further improve resolution.

There is a demand for presenting the user with the position of an organ, particularly, a lung field region in which a pulmonary blood flow needs to be present such that the user easily understands the lung field region in comparison with an X-ray image (original image).

In a blood flow, it is known that a pulmonary blood flow is gradually reduced as it becomes closer to a peripheral part of the lung field. The position of the periphery of the lung field region is recognized to determine whether a reduction in pulmonary blood flow is normal or abnormal due to any disease.

Figure 17:
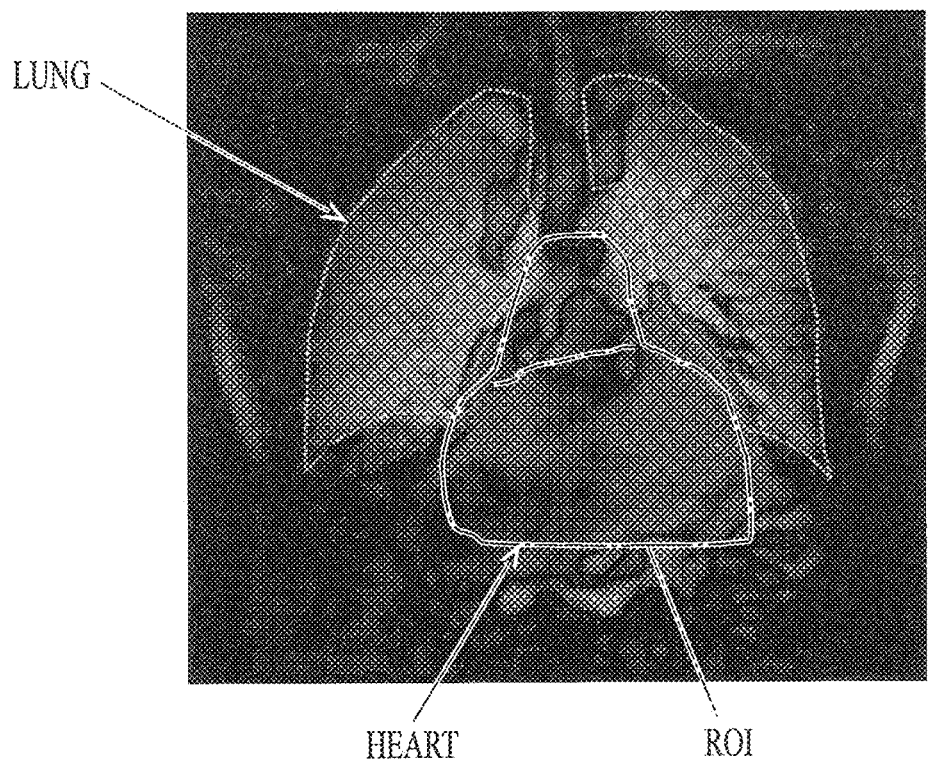
FIG. 17 is a diagram illustrating an example in which structures in the blood flow analysis image are surrounded by frames.

Therefore, for example, it is desirable to draw the position of the periphery of the lung field region with a line (a dashed line in FIG. 16A and FIG. 17) as illustrated in FIG. 16A or FIG. 17. For example, it is considered that the position is drawn as auxiliary information using the value of G among R, G, and B.

It is important to compare with an X-ray image (original image) at the time of diagnosis based on the comprehensive judgment. Therefore, it is desirable that the original image and the blood flow analysis image (the difference image or the ratio value image in this embodiment) or the functional image are displayed side by side on the display 34.

The invention is not limited to a case in which the original image and the blood flow analysis image or the functional image are separately displayed. The blood flow analysis image or the functional image may be displayed so as to be superimposed on the original image.

In this case, it is preferable that the functional image is superimposed on the original image such that a color component of the functional image is transmitted in order to improve visibility.

Specifically, for example, a method is considered which replaces one pixel with the pixel value of the functional image in units of several pixels around the original image. However, for example, a general transmission processing method may be used.

Two images are mixed and the pure visibility of the functional image is slightly reduced by the above-mentioned display. However, the comparison between the original image and the functional image can be spatiotemporally understood at a glance and the efficiency of diagnosis is improved.

The display controller 55 may display not only a still image but also a moving image on the display 34.

In a case in which blood flow analysis is displayed as a moving image, for example, if a blood vessel is blocked, a temporal change in blood volume, such as where a blood flow reaches the lung blood vessel or where the blood flow is blocked, can be displayed in an easy-to-understand manner. The user observes the moving image while comparing with the image of a healthy person to more clearly understand the difference between the case of a disease and the healthy person.

In general, pulmonary blood flows from the pulmonary hilum to a peripheral part of the lung field. In contrast, in a case in which a blood flow is different from this flow, there is a concern that an artifact will be present. For this reason, it is desirable that a moving image is displayed for blood flow analysis. In this case, it possible to easily recognize abnormality and to enable a diagnostician to appropriately recognize the abnormality.

For example, in a case in which the movement of a structure in the left-right direction is an artifact, there is a problem that positive and negative signals with the same level are added in the vicinity of the ends of the movement range of the structure in the left-right direction.

For example, in a case in which the whole body moves and shakes laterally, red and blue false signals may be generated in the periphery of the outer thorax or the lateral edge of the body in which the density of the pixel value is rapidly changed. Therefore, in a case in which blood flow analysis is displayed as a moving image, the doctor can observe the position where the false signals are generated or a temporal change in the signals and can determine whether there is an artifact. As a result, it is possible to prevent misdiagnosis.

As the display frame range of the moving image, all of the frames of the captured moving image may be displayed on the display 34. However, since the reliability of the calculation result is not secured for the frame range in which a transient response generated by the filtering process is large, it is desirable to remove the frame range in a case in which the frame range is displayed as a moving image on the display 34.

In a case in which the captured moving image and the original moving image (X-ray dynamic image) are displayed side by side, it is desirable to display the same frame range in parallel. Alternatively, all frames may be selected by, for example, the scroll bar and the reproduction of the moving image may be limited to the effective range of the filtering process.

As another display frame range, a range of N cardiac cycles which has frame images with the same heartbeat phase as the reference frame image as a start frame and an end frame may be used as the display frame range. In this case, N is an integer.

This configuration makes it possible to understand a change in a series of changes in blood flow in the cardiac cycle and makes it easy for the diagnostician to understand the changes, which is preferable.

It is preferable that a frame image corresponding to the ventricular end-systolic phase is used as a start frame and an end frame. In this case, it is possible to easily understand a series of flows from the pumping of blood from the ventricle to the pumping of blood into the ventricle.

Further, as another display frame range, only one representative cardiac cycle may be displayed. As such, the moving image reproduction time is reduced to improve the efficiency of diagnosis. In this case, the frame image that is further away from the reference frame image in terms of time is more affected by, for example, a body motion component. Therefore, it is desirable that the representative is one cycle including the reference frame image. This configuration makes it possible to minimize the influence of, for example, the body motion component.

In this embodiment, in a case in which still images are presented, it is necessary to select one representative still image from the moving image. In this case, it is desirable to select one still image corresponding to the ventricular end-systole or the time when a blood flow is maintained in the entire lung field on the basis of the heartbeat phase.

In this case, it is easiest to understand the position where the amount of pulmonary blood is reduced, using only one still image. In addition, in a case in which there is data of a plurality of cardiac cycles, a cycle after or before the reference frame image may be selected. In this case, it is possible to minimize the influence of, for example, a body motion component.

Further, it is desirable that one frame image representing the frame images included in the display frame range of the moving image is selected. In this case, the time of the representative still image in the moving image can be matched.

The display controller 55 according to this embodiment may control the displaying of the display 34 such that regions other than the diagnosis target in the blood flow analysis image or the functional image are not displayed.

In a case in which a wide range is displayed, components other than a change in blood flow volume, such as body motion components, are likely to be generated as artifacts in the range, which may cause misdiagnosis. In addition, since the diagnostician sees unnecessary signals, the efficiency of diagnostic is reduced.

Therefore, the configuration in which the regions other than the diagnosis target are not displayed makes it possible to prevent misdiagnosis. In addition, a display target is narrowed to improve the efficiency of diagnosis.

For example, in a case in which it is desired to visually recognize a lung blood flow, only the lung field region may be displayed. In this case, the user can visually recognize a pulmonary blood flow distribution while concentrating on the pulmonary blood flow distribution. In this case, regions other than the lung field region may be represented by "no signal", that is, may be displayed in black. Further, it is preferable that the heart is also included in the display region. In this case, it is possible to compare a change in blood flow volume between the lung field and the heart.

For example, the aortic region is a blood flow of the whole body system, but is not an artifact. Therefore, the aortic region may be included in the display region.

Conversely, in a case in which the user wants to view the blood flow of the whole body system, the lung field region may be excluded from the display.

In a case in which the user wants to recognize both the lung field region and the whole body system or wants to recognize artifacts, both the lung field region and the whole body system may be displayed.

As such, the configuration in which the display region and the display target can be switched according to the purpose of blood flow analysis makes it possible to perform more appropriate diagnosis according to the purpose.

For Operation of Analysis Apparatus (Dynamic Image Analysis Apparatus)

Next, the operation of the analysis apparatus 3 which is the dynamic image analysis apparatus according to this embodiment will be described with reference to FIG. 18.

First, in a case in which the imaging apparatus 1 captures a dynamic image, the image acquirer 51 of the hardware processor 31 in the analysis apparatus 3 receives data of the dynamic image (X-ray dynamic image) including a plurality of frame images through the communication network NT (Step 51). The dynamic image acquired by the image acquirer 51 may be all images captured by the imaging apparatus 1. In this embodiment, it is preferable that the dynamic image is a frame image with little breathing and body motion, such as a frame image captured in a breath-hold state or frame images around the frame image. In this case, it is possible to avoid accumulating images that are not suitable for blood flow analysis in the analysis apparatus 3 and thus to reduce, for example, the load of the storage 32 of the analysis apparatus 3.

For example, in a case in which the imaging console 2 has calculated an analysis target frame range, the image acquirer 51 also acquires information of the analysis target frame range so as to be associated with the dynamic image data.

In a case in which the dynamic image is acquired, the hardware processor 31 (the blood flow analyzer 54 of the hardware processor 31) divides the image into small blocks (Step S2). The image is divided into small blocks and the representative value of each block is calculated, which makes it possible to reduce the influence of white noise or movement.

The logarithmic conversion processor 53 of the hardware processor 31 performs a logarithmic conversion process for the original image (original X-ray dynamic image) (Step S3). Therefore, it is possible to measure a temporal change in the thickness of a material.

The blood flow analyzer 54 of the hardware processor 31 performs a noise removal process of applying a filter, such as a high-pass filter (for example, 0.8 Hz) or a bandpass filter (cardiac cycle) in the time direction in order to reduce the influence of, for example, movement caused by a body motion (Step S4).

The analysis target setter 52 of the hardware processor 31 sets a frame image acquired at a predetermined timing, such as a frame image corresponding to the ventricular end-diastole of the heart, as the reference frame image (Step 55). As described above, which of the frame images captured at any point of time (timing) is set as the reference frame image is appropriately determined according to the purpose of blood flow analysis, such as the part to be subjected to blood flow analysis.

Then, the blood flow analyzer 54 of the hardware processor 31 calculates the difference (or the ratio) between the reference frame image and a frame image (comparative frame image) that is different from the reference frame image and is to be compared with the reference frame image and generates a blood flow analysis image according to the difference value (or the ratio value) (Step S6).

The display controller 55 controls the display 34 such that the blood flow analysis image generated by the blood flow analyzer 54 is appropriately displayed on a display screen of the display 34.

In this case, the blood flow analysis image and the original X-ray image may be displayed side by side on the display 34 or the blood flow analysis image may be displayed on the display 34 so as to be superimposed on the original X-ray image. In addition, the blood flow analysis image may be a difference image based on the difference value (or a ratio value image based on the ratio value) or may be a functional image obtained by performing color coding on the basis of, for example, the density value of the image.

According to this embodiment, it is possible to perform blood flow analysis on the basis of the dynamic image (X-ray dynamic image) which can be relatively simply obtained in a non-invasive manner for a patient that is the object M.

The procedure of the process illustrated in FIG. 18 is an example and, for example, the sequence of the process is not limited to the above.

In the procedure illustrated in FIG. 18, it is possible to set the reference frame image on the basis of the waveform after the filtering process. However, the invention is not limited to a case in which the reference frame image is set on the basis of the waveform after the filtering process.

The process of dividing an image into small blocks and the filtering process are appropriately performed in order to remove noise and are not essential. For example, only one or the processes may be performed or neither of the processes may be performed.

Effects

As described above, the analysis apparatus 3 which is the dynamic image analysis apparatus according to this embodiment includes:

the image acquirer 51 that acquires a dynamic image (X-ray dynamic image) including a plurality of continuous frame images acquired by continuously capturing a living body having a heartbeat in time series;

the logarithmic conversion processor 53 that performs logarithmic conversion for a pixel value of the dynamic image acquired by the image acquirer 51 to create a logarithmically converted image;

the analysis target setter 52 that sets, as a reference frame image, one frame image based on the heartbeat phase in at least one of the dynamic image or the logarithmically converted image; and the blood flow analyzer 54 that calculates the difference or ratio between the reference frame image and a comparative frame image which is another frame image and generates a blood flow analysis image on the basis of the difference.

As such, in this embodiment, since blood flow analysis is performed using the dynamic image, for example, the blood flow analysis can be relatively simply performed using a general apparatus, as compared to the blood flow scintigraphic examination according to the related art. Since it is only necessary to capture normal dynamic images, the examination is made in a non-invasive manner, X-ray exposure is relatively small, and the burden on the patient is reduced.

The result of blood flow analysis having the same reliability as other examinations including a blood flow scintigraphic examination can be obtained by the method that reduces the burden on the patient.

In this embodiment, the analysis target setter 52 detects movement that becomes a blood flow artifact from the frame images and selects the reference frame image and the comparative frame image in the range in which frame images without including movement that becomes the blood flow artifact among a plurality of frame images are continuous.

Therefore, it is possible to perform analysis using the frame image suitable for blood flow analysis and to obtain the result of the flow analysis result with higher accuracy.

In this embodiment, in a case in which the difference or ratio between the reference frame image and the comparative frame image is calculated, the blood flow analyzer 54 uses each pixel value as the representative value of a block size that is equal to or greater than 7 mm.

As such, in a case in which an image is divided into small blocks and the representative value of the small block is calculated, it is possible to appropriately remove, for example, white noise.

Since the block size is set to a value that is greater than the diameter of the blood vessel and the movement width of the blood vessel, it is possible to prevent the blood vessel from coming in and out of the block range and to control the occurrence of artifacts caused by the movement of the blood vessel.

In this embodiment, in a case in which the difference or ratio between the reference frame image and the comparative frame image is calculated, the blood flow analyzer 54 performs the filtering process of limiting a frequency component in the time direction for each pixel value.

The performance of the filtering process makes it possible to remove noise from the image, to reduce the influence of, for example, movement caused by a body motion, and to perform blood flow analysis with higher reliability.

In this embodiment, the analysis target setter 52 sets a frame image corresponding to various timings in the heartbeat phase as the reference frame image according to, for example, the object to be subjected to blood flow analysis or the purpose of the blood flow analysis.

For example, in a case in which the analysis target setter 52 sets a frame image corresponding to the ventricular end-diastole of the heart as the reference frame image, the analysis target setter 52 can set, as the reference frame image, a frame image captured at the timing when the largest amount of blood flows into the heart and the smallest amount of blood is pumped to other organs.

Therefore, in blood flow analysis in which a change in pixel value caused by a change in blood volume is very small, it is possible to prevent the change in pixel value to be analyzed from being buried in various types of noise and thus to relatively accurately perform measurement.

It is possible to minimize the influence of the subtle shift of the heartbeat phase in each part.

Further, the use of this method makes it easy to obtain information close to the result of the blood flow scintigraphic examination whose reliability has already been ensured as an image and to verify the correctness of the analysis result.

For example, in a case in which the analysis target setter 52 sets a frame image corresponding to the ventricular systole of the heart after a heartbeat is generated as the reference frame image, it is possible to observe a change in blood volume before the blood pumped from the heart reaches a peripheral blood vessel.

Therefore, it is possible to minimize the influence of movement caused by the beating of the heart and to accurately recognize the distribution of a change in the blood volume of a thin blood vessel such as a peripheral blood vessel.

For example, in a case in which the analysis target setter 52 sets the reference frame image on the basis of a change in the density of a region of the lung field in the vicinity of the heart or a change in the position of a blood vessel, such as the aorta, it is possible to accurately calculate the heartbeat phase of the ventricle.

In this embodiment, the analysis apparatus further includes:

the display 34 that displays a difference image based on the difference between the reference frame image and the comparative frame image calculated by the blood flow analyzer 54 (or a ratio value image based on the ratio between the reference frame image and the comparative frame image) as a functional image; and the display controller 55 that controls the displaying of the display 34.

The display controller 55 controls the displaying of the display 34 such that colors vary according to whether the pixel value of the difference image (or the ratio value image) is positive or negative, and performs control such that the absolute value of the difference value (or the ratio value) is reflected in the displaying of the display 34 so as to be associated with parameters other than the color.

This configuration makes it possible to present the state of a blood flow such that the state is visibly easy to understand and to provide the doctor with images useful for diagnosis.

The parameters other than the color include at least one of the intensity, saturation, and brightness of colors and a combination thereof.

Therefore, it is possible to clearly show the part in which a blood flow volume is large and the part in which a blood flow volume is small.

In this embodiment, the display controller 55 controls the displaying of the display 34 such that regions other than the diagnosis target in the functional image are not displayed.

As such, since the regions other than the diagnosis target are not displayed, it is possible to prevent misdiagnosis. In addition, the display target is narrowed to improve the efficiency of diagnosis. Further, in a case in which there is no artifact in a diagnosis target part and there are artifacts in other parts, the diagnosis target part can be used for diagnosis and it is possible to ensure a large amount of data used for diagnosis.

MODIFICATION EXAMPLES

The invention is not limited to the above-described embodiment and may be appropriately modified without departing from the scope of the invention.

For example, in this embodiment, a case in which the analysis apparatus 3 which is a dynamic image analysis apparatus includes the display 34 that displays, for example, the blood flow analysis image has been described above. However, it is not essential that the analysis apparatus 3 includes the display 34.

For example, a display device including a high-resolution monitor may be provided separately from the analysis apparatus 3 such that the analysis result (that is, for example, the blood flow analysis image) of the analysis apparatus 3 can be checked by the monitor such as the display device.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-138096, filed on Jul. 24, 2018, is incorporated herein by reference in its entirety.

What is claimed is:

1. A dynamic image analysis apparatus comprising:
a hardware processor that:
acquires an X-ray dynamic image including continuous frame images acquired by continuously capturing a living body having a heartbeat in time series;
performs logarithmic conversion for a pixel value of the acquired X-ray dynamic image to create a logarithmically converted image;
sets, as a reference frame image, one frame image based on a heartbeat phase in at least one of the X-ray dynamic image and the logarithmically converted image;
calculates (i) a difference or ratio between the X-ray dynamic image as the reference frame image and another X-ray dynamic image as a comparative frame image which is another frame image or (ii) a difference or ratio between the logarithmically converted image as the reference frame image and another logarithmically converted image as the comparative frame image; and
generates a blood flow analysis image based on the difference or the ratio,
wherein the hardware processor:
detects movement that becomes a blood flow artifact from the frame images; and
selects the reference frame image and the comparative frame image from a range in which frame images without including the movement that becomes the blood flow artifact among the frame images are continuous.

2. The dynamic image analysis apparatus according to claim 1, wherein the hardware processor sets a frame image corresponding to a ventricular end-diastole of a heart as the reference frame image.

3. The dynamic image analysis apparatus according to claim 1, wherein the hardware processor uses each pixel value as a representative value of a block size that is equal to or greater than 7 mm when the hardware processor calculates the difference or ratio between the reference frame image and the comparative frame image.

4. The dynamic image analysis apparatus according to claim 1, wherein the hardware processor performs a filtering process of limiting a frequency component in a time direction for each pixel value when the hardware processor calculates the difference or ratio between the reference frame image and the comparative frame image.

5. The dynamic image analysis apparatus according to claim 1, wherein the hardware processor sets, as the reference frame image, a frame image corresponding to a ventricular systole of a heart after the heartbeat is generated.

6. The dynamic image analysis apparatus according to claim 1, wherein the hardware processor sets the reference frame image based on a change in density of a region of a lung field in a vicinity of a heart or a change in a position of a blood vessel.

7. The dynamic image analysis apparatus according to claim 1, further comprising:
a display that displays, as a functional image, the blood flow analysis image obtained by calculating the difference or ratio between the reference frame image and the comparative frame image,
wherein
the hardware processor controls displaying of the display, and
the hardware processor (i) controls the displaying of the display such that colors vary according to whether a pixel value of the functional image is positive or negative, and (ii) performs control such that an absolute value of the pixel value is reflected in the displaying of the display so as to be associated with parameters other than color.

8. The dynamic image analysis apparatus according to claim 7, wherein the parameters other than color include at least one of saturation, brightness, and a combination of the saturation and the brightness.

9. The dynamic image analysis apparatus according to claim 7, wherein the hardware processor controls the displaying of the display such that a region other than a diagnosis target in the functional image is not displayed.

10. A dynamic image analysis method comprising:
an image acquisition step of acquiring an X-ray dynamic image including continuous frame images acquired by continuously capturing a living body having a heartbeat in time series;
a logarithmic conversion processing step of performing logarithmic conversion for a pixel value of the X-ray dynamic image acquired in the image acquisition step to create a logarithmically converted image;
an analysis target setting step of setting, as a reference frame image, one frame image based on a heartbeat phase in at least one of the X-ray dynamic image and the logarithmically converted image; and
a blood flow analysis step of:
calculating (i) a difference or ratio between the X-ray dynamic image as the reference frame image and another X-ray dynamic image as a comparative frame image which is another frame image or (ii) a difference or ratio between the logarithmically converted image as the reference frame image and another logarithmically converted image as the comparative frame image; and
generating a blood flow analysis image based on the difference or the ratio,
wherein the dynamic image analysis method further comprises:
detecting movement that becomes a blood flow artifact from the frame images; and
selecting the reference frame image and the comparative frame image from a range in which frame images without including the movement that becomes the blood flow artifact among the frame images are continuous.

11. A non-transitory computer readable recording medium storing a program that causes a computer of a dynamic image analysis apparatus to implement:
an image acquisition function of acquiring an X-ray dynamic image including continuous frame images acquired by continuously capturing a living body having a heartbeat in time series;
a logarithmic conversion processing function of performing logarithmic conversion for a pixel value of the X-ray dynamic image acquired by the image acquisition function to create a logarithmically converted image;

an analysis target setting function of setting, as a reference frame image, one frame image based on a heartbeat phase in at least one of the X-ray dynamic image and the logarithmically converted image; and a blood flow analysis function of:
  calculating (i) a difference or ratio between the X-ray dynamic image as the reference frame image and another X-ray dynamic image as a comparative frame image which is another frame image or (ii) a difference or ratio between the logarithmically converted image as the reference frame image and another logarithmically converted image as the comparative frame image; and
  generating a blood flow analysis image based on the difference or the ratio, wherein the computer of the dynamic image analysis apparatus further implements;
  a detecting function of detecting movement that becomes a blood flow artifact from the frame images, and
  a selecting function of selecting the reference frame image and the comparative frame image from a range in which frame images without including the movement that becomes the blood flow artifact among the frame images are continuous.

* * * * *